(12) United States Patent
Kitzhoffer et al.

(10) Patent No.: US 7,421,885 B2
(45) Date of Patent: Sep. 9, 2008

(54) METHOD FOR CHARACTERIZING POROUS LOW DIELECTRIC CONSTANT FILMS

(75) Inventors: Ronald Joseph Kitzhoffer, Easton, PA (US); Scott Jeffrey Weigel, Allentown, PA (US); Charles Gardner Coe, Macungie, PA (US); Michael Francis Kimak, Allentown, PA (US); James Edward MacDougall, New Tripoli, PA (US); John Francis Kirner, Orefield, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 331 days.

(21) Appl. No.: 11/168,907

(22) Filed: Jun. 28, 2005

(65) Prior Publication Data

US 2006/0005608 A1   Jan. 12, 2006

Related U.S. Application Data

(60) Provisional application No. 60/583,924, filed on Jun. 28, 2004.

(51) Int. Cl.
G01N 15/08  (2006.01)
(52) U.S. Cl. .................... 73/38; 73/866; 702/43; 702/82
(58) Field of Classification Search .............. 73/38, 73/866; 702/43, 82
See application file for complete search history.

(56) References Cited

U.S. PATENT DOCUMENTS 6,662,631 B2 * 12/2003 Baklanov et al. ............. 73/38

| | | | |
|---|---|---|---|
| 7,016,028 B2 * | 3/2006 | Holsteyns et al. | 356/237.1 |
| 2002/0030297 A1 * | 3/2002 | Gallagher et al. | 264/49 |
| 2002/0042020 A1 * | 4/2002 | Gallagher et al. | 430/272.1 |
| 2003/0094032 A1 * | 5/2003 | Baklanov et al. | 73/38 |
| 2003/0224544 A1 * | 12/2003 | Prisco et al. | 438/16 |

OTHER PUBLICATIONS

Hata, Negoro, Takada, Xiao, Yamada and Kikkawa, "Integrated Characterization of Porous Low-k Films for Identifying Killer Pores and Micropores", Jun. 2-4, 2003. http://ieeexplore.ieee.org/xpls/abs_all.jsp?arnumber=1219710 accessed: Feb. 17, 2007.*

(Continued)

Primary Examiner—Hezron E. Williams
Assistant Examiner—Samir M. Shah
(74) Attorney, Agent, or Firm—Rosaleen P. Morris-Oskanian

(57) ABSTRACT

A method and apparatus for determining pore size distribution and/or the presence of at least one killer pore in at least a portion of a porous film deposited upon a substrate are disclosed herein. In one embodiment, there is provided a method for determining pore size distribution comprising: providing the substrate having the film deposited thereupon wherein the film comprises pores and wherein the pores have a first volume; exposing the film to an adsorbate at a temperature and a pressure sufficient to provide condensation of the adsorbate in pores and wherein the pores after the exposing step have a second volume; and measuring the difference between the first and the second volume using a volumetric technique; and calculating the pore size and pore volume using the change in the first and the second volume, the pressure, and a model that relates pressure to pore diameter.

6 Claims, 12 Drawing Sheets

OTHER PUBLICATIONS

"Characterization of Porous Low-k Dielectric Constant Thin Films", NIST, Polymers Division, Author unknown, Date unknown. http://polymers.nist.gov/projects/project-detail.cfm?PID=11 accessed: Dec. 17, 2007.*

Grosso, D., "Two-Dimensional Hexagonal Mesoporous Silica Thin Films Prepared from Block Copolymers: Detailed Characterization and Formation Mechanism", Chem. Mater. 2001, 13, pp. 1848-1856.

Ayral, A., "Porosity of sol-gel derived silica coatings on glass substrates", Journal of Materials Science Letters, 17 (1998), pp. 883-885.

Everett, D. H., "Manual of Symbols and Terminology for Physocochemical Quantities and Units," Appendix II, Part I, International Union of Pure and Applied Chemistry, pp. 1-78 (1971).

Iacoponi, J., "Status and Future Prospects for Low k Interconnect Metrology," International SeMatech, pp. 1-46 (2003).

Barrett, E. P., et al., "The Determination of Pore Volume and Area Distributions in Porous Substances. I. Computations from Nitrogen Istherms," *The Volume and AreaDistributions in Porous Substances*, pp. 373-380 (1951).

Cohan, L. H., "Sorption Hysteresis and the Vapor Pressure of Concave Surfaces," *Sorption Hysteresis and Vapor Pressure of Concave Surfaces*, pp. 433-435 (1938).

Ohkubo, T., et al., "Adsorption Properties of Templated Mesoporous Carbon (CMK-1) for Nitrogen and Supercritical Methane—Experiment and GCMC Simulation," *J. Phys. Chem. B*, 106, pp. 6523-6528 (2002).

Kruk, M., et al., "New Approach to Evaluate Pore Size Distributions and Surface Areas for Hydrophobic Mesoporous Solids," *J. Phys. Chem B.*, 103, pp. 10670-10678 (1999).

Jaroniec, M., et al., "Standard Nitrogen Adsorption Data for Characterization of Nanoporous Silicas," *Langmuir*, 15, pp. 5410-5413 (1999).

Groen, J. C., et al., "Pore Size Determination in Modified Micro- and Mesoporous Materials. Pitfalls and Limitations in Gas Adsorption Data Analysis," *Elsevier, microporous and Mesoporous Materials*, 60, pp. 1-17 (2003).

Frye, G.C., et al., "Characterization of the Surface Area and Porosity of Sol-Gel Films Using Saw Devices," *Mat. Res. Soc. Symp. Proc.*, vol. 121, pp. 349-354 (1988).

Cranston, R. W., et al., "The Determination of Pore Structures from Nitrogen Adsorption Isotherms," *Proceedings of the International Congress on Catalysis, Advances in Catalysis and Related Subjects*, vol. IX, pp. 143-154 (1957).

Harkins, W. D., et al., "An Adsorption Method for the Determination of the Area of a Solid Without the Assumption of a Molecular Area, and the Area Occupied by Nitrogen Molecules on the Surfaces of Solids," *Letters to the Editor*, pp. 431-432 (1943).

Halsey, G., "Physical Adsorption of Non-Uniform Surfaces," *The Journal of Chemical Physics*, vol. 16, No. 10, pp. 931-937 (1948).

Brunauer, S., et al., "Pore Structure Analysis Without a Pore Shape Model," *Journal of Colloid and Interface Science*, 24, pp. 451-463 (1967).

D. Dollimore et al, An improved method for the calculation of pore size distribution from adsorption data, J. Appl. Chem., Mar. 1964, 14, pp. 109-114.

N. Hata et al, A new approach of thin-film x-ray diffraction/scattering analysis for ultra-low-k dielectrics with periodic pore structure, Mat. Res. Soc. Symp. Proc. 2002, vol. 716, pp. B12.5.1-B12.5.6.

* cited by examiner

METHOD FOR CHARACTERIZING POROUS LOW DIELECTRIC CONSTANT FILMS

CROSS-REFERENCE TO RELATED APPLICATIONS

This application claims the benefit of U.S. Provisional Application No. 60/583,924, filed 28 Jun. 2004.

BACKGROUND OF THE INVENTION

There is a continuing desire in the microelectronics industry to increase the circuit density in multilevel integrated circuit devices such as memory and logic chips in order to improve the operating speed and reduce power consumption. In order to continue to reduce the size of devices on integrated circuits, it has become necessary to use insulators having a low dielectric constant (k) to reduce the resistance-capacitance ("RC") time delay of the interconnect metallization and to prevent capacitive crosstalk between the different levels of metallization. Such low dielectric materials are desirable for premetal dielectric layers and interlevel dielectric layers.

Typical dielectric materials for devices with 180 nm line width are materials with a dielectric constant between about 3.8 and 4.2. As the line width decreases, the dielectric constant should also be decreased. For example, devices with 130 nm line width require materials with a dielectric constant between about 2.5 and 3.0. Extremely low dielectric constant ("ELK") materials generally have a dielectric constant between about 2.0 and 2.5. Devices with 90 nm line width require materials with dielectric constants less than 2.4.

One approach to lowering the dielectric constant of interlevel dielectrics used in integrated circuit manufacture is to introduce porosity into the film. However, as the pore size approaches the dimensions of the features on the chip, the probability for failure increases. It is desirable to keep the pore dimensions smaller than the lateral dimensions or feature size in the interlayer dielectric films in order to minimize defects due to shorting via metal ion migration or dielectric breakdown. Typically, the metal migration is caused by defects in the barrier layers, which allow copper to diffuse into the dielectric layer. With more advanced barrier schemes, the IC manufacturers want to use CVD methodologies with smaller molecular precursors to deposit the barrier layer, therefore the pore size in the dielectric film should be small enough to insure that the barrier itself will not diffuse into the porous structure. The term "killer pores", as used herein, describes pores that that can cause catastrophic failure. Because these defects may result in production loss, there is a need for measuring the pore size distribution for low κ films used for interlevel dielectrics.

Historically, volumetric and gravimetric adsorption techniques have been extremely valuable for characterizing the pore size and pore volume of mesoporous materials in the form of powders. Static volumetric adsorption techniques are those in which quantities of adsorbate gas are admitted from a manifold to an attached adsorption cell holding the sample at a controlled temperature, and the amounts of gas adsorbed at equilibrium are calculated using mass balance equations from the measured pressures before and after the dose is delivered, the free space values for the manifold and the sample holder, and appropriate gas equations of state. Gravimetric adsorption techniques are those in which the amounts of gas adsorbed at controlled pressures and temperatures are measured by the change in weight of the sample. The adsorption isotherm is converted to a pore size distribution using a model for capillary condensation that relates the pressure of adsorption to the size of the pores. However, these techniques may be difficult to use when the materials are in the form of thin films on substrates such as a silicon wafers. These thin films have too small a total pore volume and surface area to provide sufficient sorption for analysis by volumetric or gravimetric adsorption. Consequently, certain porosimetric techniques, such as $N_2$ adsorption, mercury intrusion, or quartz crystal microbalances, may lack the sensitivity to characterize porosity in films that are less than 1 μm thick and attached to a 1-mm-thick silicon single-crystal wafer.

To remedy this, films are scraped off several substrates or wafers to provide a sufficient sample for analysis. Scraping the film off the substrate, however, could alter the pore size distribution. Further, when the pore size distribution is determined by adsorption techniques involving capillary condensation, the resulting powder can generate "phantom" porosity because of a sharp upturn in the isotherm at high relative pressure ($P/P_0$) resulting from capillary condensation in the interstices between the powder particles. This phantom porosity cannot be distinguished from the presence of large pores in the pore size distribution calculations that would be attributed to killer pores. Consequently, there is a need for characterizing the film while still on the wafer in order to determine whether killer pores are present in the film.

Even when adsorption techniques are used to characterize the film on the wafer, the adsorption isotherm typically has a gradual positive slope at high relative pressures. It is not clear whether the gradual slope in the isotherm is caused by adsorption in pores having a large diameter. However, when classical models for capillary condensation are used to convert the adsorption isotherm to a pore size distribution, this gradual uptake at high $P/P_0$ is ascribed to uptake by larger pores. The use of classical models may limit the sensitivity to the absence of killer pores. Thus, there is a need for higher sensitivity to the absence of killer pores, or "a lower killer pore volume absence detection limit" as used herein.

Several advanced non-destructive methods have been pursued by the semiconductor industry that measure the porosity of the film while still on the wafer as an alternative to the aforementioned analytical methods. Some of these alternative techniques use a beam of radiation rather than adsorption. Positronium annihilation lifetime spectroscopy ("PALS") correlates the pore size with the lifetime of positronium ("Ps" which is the electron bound state with its antiparticle the positron), which is created when a beam of positrons is focused on the film, and which decays through collisions with bound electrons in the pore walls. PALS requires a positron beam source and gamma ray detector. In addition, films with open connected porosity may need to be capped with a non-porous layer prior to PALS analysis.

In other techniques such as small-angle neutron scattering ("SANS") and small-angle X-ray scattering ("SAXS"), an average chord length or pore size is mathematically extracted from the plot of scattering intensity versus scattering vector using a model for the void and solid phases in the structure. More recently, radial diffuse X-ray reflectivity ("XRR") has been used to measure pore size. In the radial diffuse XRR analytical technique, a radial diffuse XRR scan is obtained at grazing incidence angles by impinging the incident X-ray beam at an angle between the critical angle of the film and the critical angle of the substrate and scanning the detector over a large range to capture scatter as a function of angle. The resulting data can be modeled to determine the pore size by, for example, using a 1- or 2-parameter model of a standard distribution of pores around the average pore diameter because of the paucity of data. The above techniques—SANS, SAXS, and XRR—use relatively sophisticated equipment to induce scattering in order to measure the pore size of the substrate on one spot of the substrate at a time. These techniques also assume a shape for the distribution of pores around an average pore diameter.

Still other alternative analytical techniques may measure the porosity of the film while still on the wafer using adsorption techniques besides volumetric or gravimetric adsorption techniques to monitor the uptake of a reference vapor or gas onto an adsorbent. In this connection, the surface acoustic waves ("SAW") technique has been used to determine the extent of adsorption of, for example, $N_2$ at 77 degrees Kelvin ("K"), on mesoporous films deposited on a special piezoelectric substrate. The SAW technique may use the change in the oscillation frequency of surface acoustic waves as a function of change in mass density to measure the amount adsorbed. Yet another technique, the ellipsometric porosimetry ("EP") technique, measures the extent of adsorption of an organic vapor, such as toluene at room temperature, by the change in the refractive index. The EP analytical technique assumes the index of refraction of a condensed liquid (e.g., toluene) in a nanoscale pore is identical to that of the bulk liquid. Although the small analytical area of less than 1 $mm^3$ may be appropriate for the microelectronic industry, particularly if it is desirable to "isolate" the presence of defects on a specific location on the wafer, it may be impractical as a quality control tool in identifying whether there are any defects present on an entire wafer. The X-ray porosimetry ("XRP") analytical technique monitors the extent of uptake of a reference fluid, such the organic vapor toluene, on exposure to the adsorbate by change in the critical angle of reflection measured by X-ray reflectivity, which depends on the change in density of the film. The XRP method requires the atomic composition of the film to convert electron density to mass density, which usually requires the use of complex techniques such as forward recoil elastic scattering and Rutherford backscattering. Calculations of pore size distribution from adsorption isotherms measured with the aforementioned analytical techniques—SAW, EP, and XRP—have traditionally used historical procedures, such as those procedures advanced by Barrett, Joyner, and Halenda, and/or classical theoretical models of capillary condensation such as the Kelvin equation.

In processes for producing porous films substrates, there may be a need for quality control testing in order to accept or reject films based on the presence of killer pores. Further, there may also be a need for process control in the film production process in order to change the parameters of the film production process based on the presence of killer pores.

All references cited herein are incorporated herein by reference in their entireties.

BRIEF SUMMARY OF THE INVENTION

The method disclosed herein, for the detection of determination of pore size distribution and/or killer pores within a porous film that is deposited upon a substrate, satisfies one, if not all, of the needs of in the art. In one aspect, there is provided a method for determining pore sizes contained within a film deposited upon a substrate comprising: providing the substrate having the film deposited thereupon wherein the film comprises pores and wherein the pores have a first volume; exposing the film to an adsorbate at a temperature and a pressure sufficient to provide condensation of the adsorbate in pores and wherein the pores after the exposing step have a second volume; and measuring the difference between the first and the second volume using a volumetric technique; and calculating the pore size and pore volume using the change in the first and the second volume, the pressure, and a model that relates pressure to pore diameter. In one embodiment, the amount adsorbed within the pores can be determined for different pressures at constant temperature, which is referred to herein as an "adsorption isotherm". In an alternative embodiment, the amount adsorbed within the pores can be determined for different temperatures at constant pressure, which is referred to herein as an "adsorption isobar".

In yet another aspect, there is provided a method for determining a presence of at least one killer pore contained within a porous film deposited upon a substrate wherein a pore size of the at least one killer pore is equal to or greater than a reference pore size comprising: providing the substrate having the film deposited thereupon wherein the film comprises pores and wherein the pores have a first volume; exposing the film to an adsorbate at a temperature and a pressure sufficient to provide condensation of the adsorbate in pores and wherein the pores after the exposing step have a second volume; measuring the difference between the first and the second volume; repeating the exposing and measuring steps wherein the condensed adsorbate has a different density than the previous exposure; calculating the pore size and volume for each exposure using the difference in the first and the second volume, the pressure, and a model that relates pressure to pore diameter and accounts for the change in density of the condensed adsorbate; obtaining a maximum pore size from the distribution; and determining the presence of at least one killer pore by comparing the maximum pore size to the reference pore size.

In a further aspect, there is provided a process for producing a porous film on a substrate comprising: providing the substrate having the film deposited thereupon wherein the film comprises pores and wherein the pores have a first volume; exposing the film to an adsorbate at a temperature and a pressure sufficient to provide condensation of the adsorbate in pores and wherein the pores after the exposing step have a second volume; measuring the difference in the first and the second volume; repeating the exposing and measuring steps wherein the condensed adsorbate has a different density than the previous exposure; calculating the pore size and volume for each exposure using the difference in the first and the second volume, the pressure, and a model that relates pressure to pore diameter and accounts for the change in density of the condensed adsorbate; obtaining a maximum pore size from the distribution; determining the presence of at least one killer pore by comparing the maximum pore size to the reference pore size; and accepting or rejecting the film based on the presence of killer pores, and/or changing the parameters of the process for producing the film based on the presence of killer pores.

Figure 6:
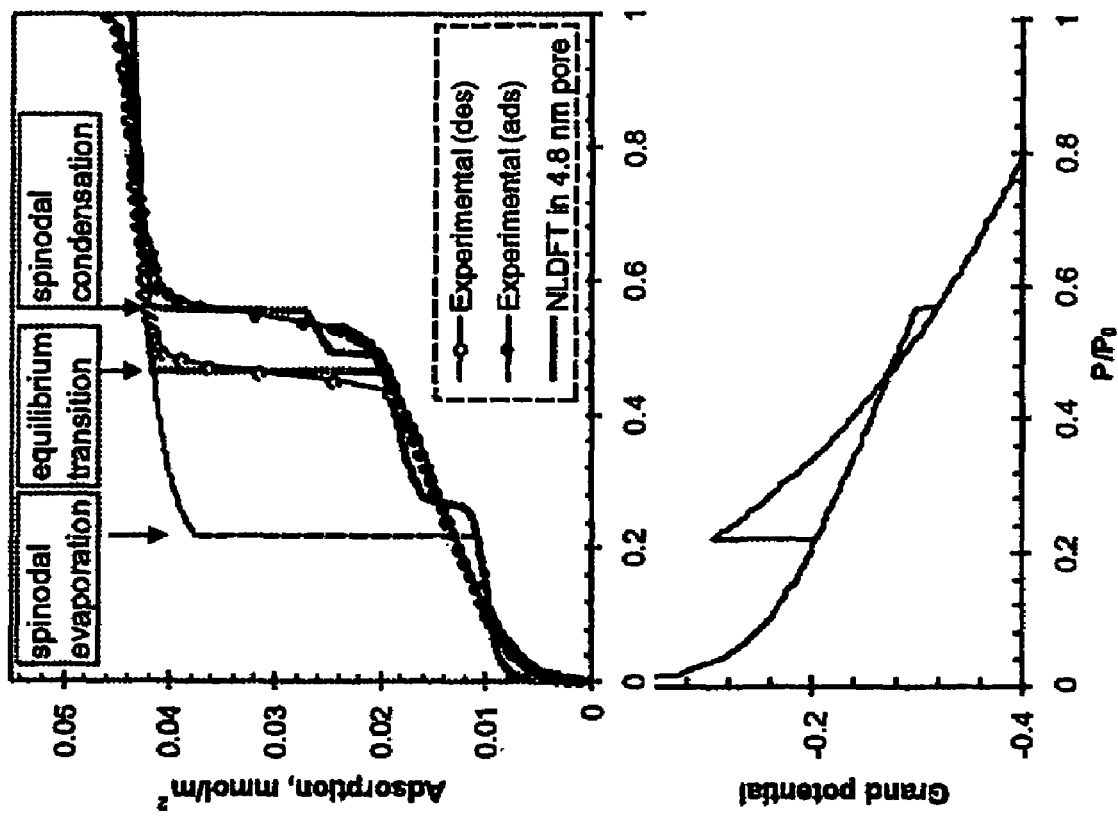
FIG. 6 provides the NLDFT calculation of adsorption of the adsorbate Argon at 87 K in a 48 angstrom cylindrical pore.

The top portion of FIG. 6 provides a comparison of the NLDFT isotherm with the corresponding experimental isotherm on an enlarged MCM-41 type material. The arrows indicate (from right to left) the relative pressures of spinodal condensation, equilibrium transition, and spinodal evaporation calculated by NLDFT. The bottom portion of FIG. 6 provides the minima in the grand potential showing that in the region of hysteresis there are two solutions depending on the starting point.

Figure 7:
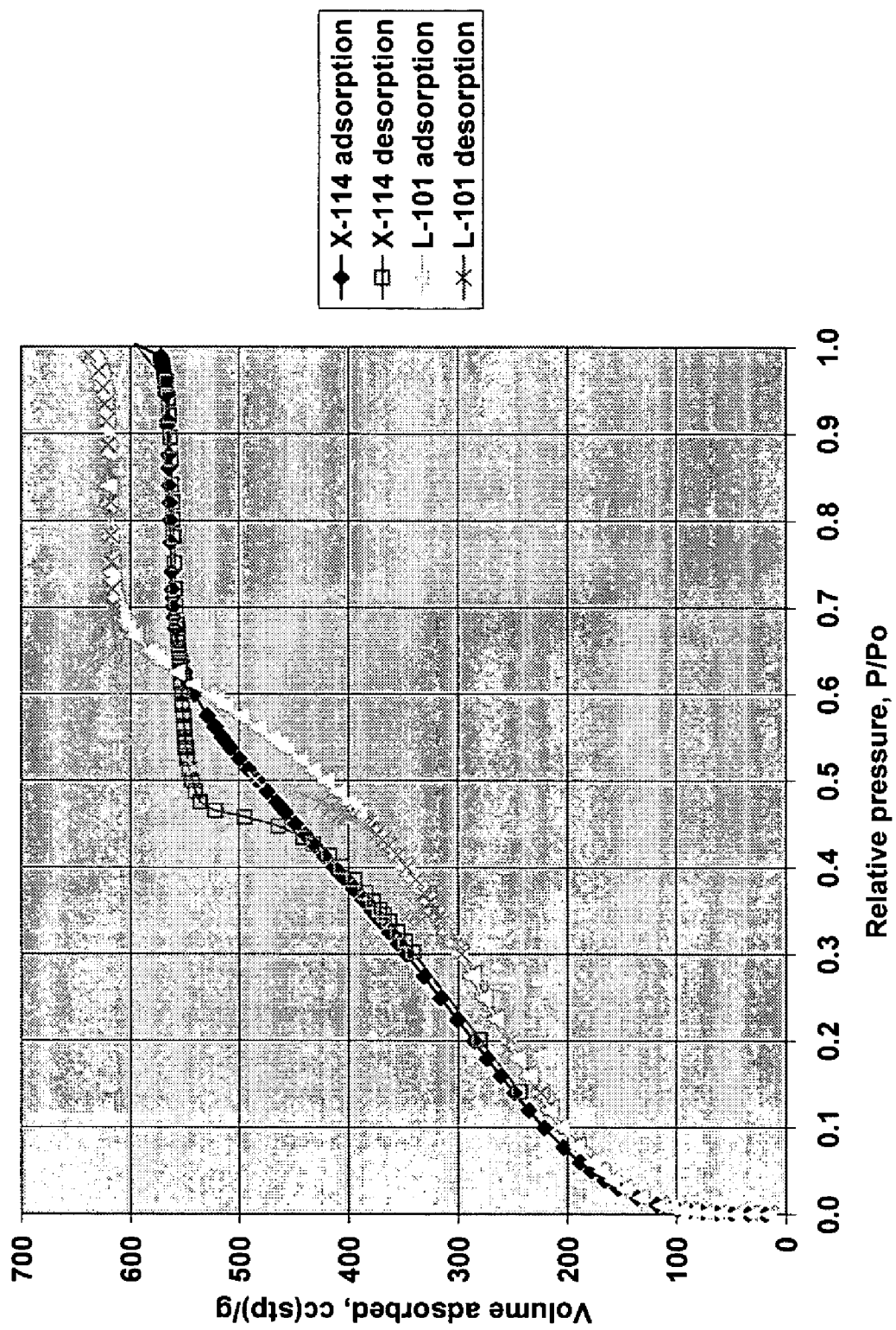

FIG. 7 provides the adsorption/desorption isotherm using a $N_2$ adsorbate at 77 K for the samples prepared in Example 1 that used Triton X-114 and Pluronic L-101 surfactants as porogens to provide porous films having dielectric constants of 1.9.

Figure 8:
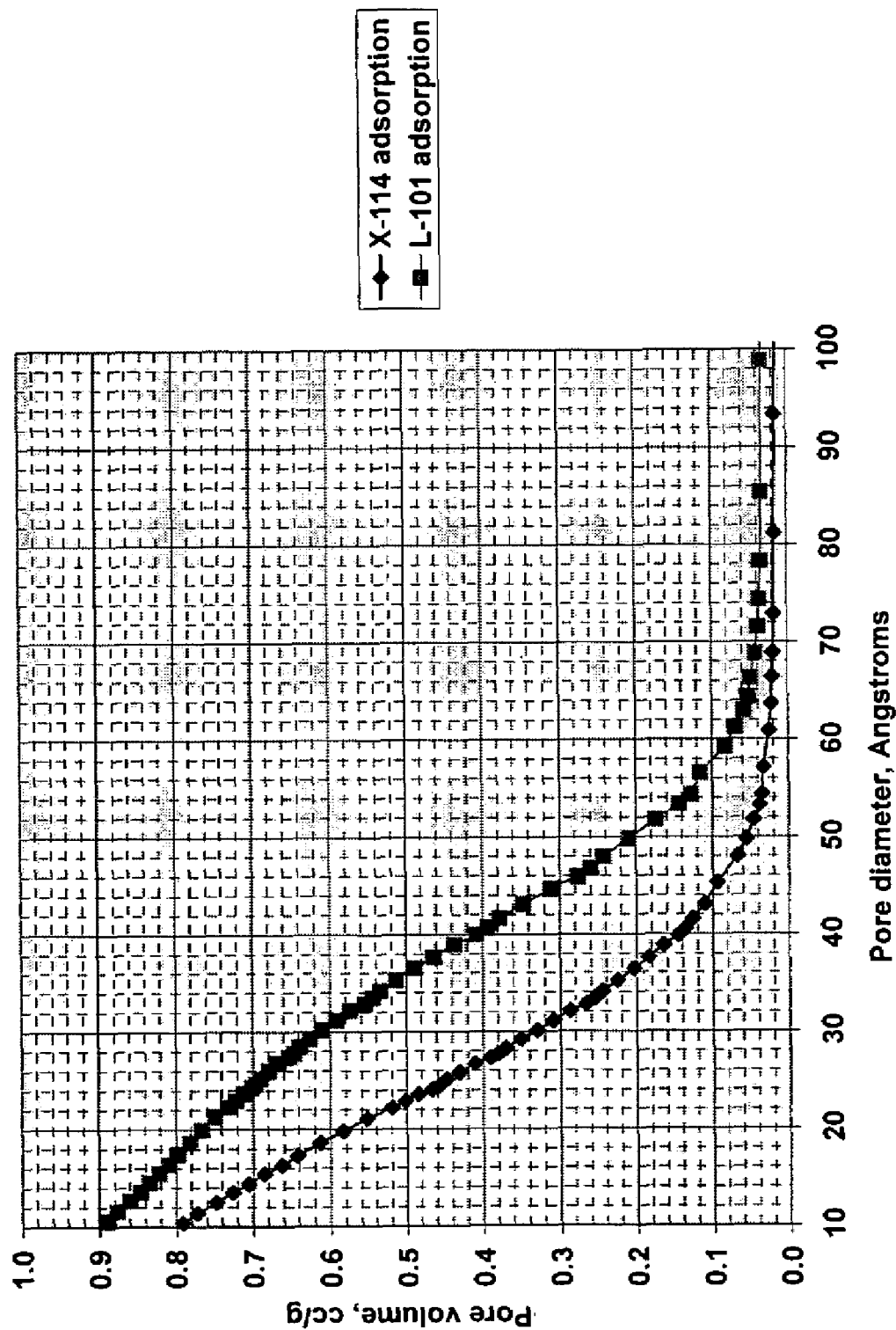

FIG. 8 provides a plot of cumulative pore volume versus pore diameter derived from ASAP BJH calculations (BJH parameters: 10-3000 Å, F=0, default ASAP Halsey) using the adsorption branch of the isotherm for $N_2$ at 77 K on low κ films prepared using Triton X-114 and Pluronic L-101 surfactants as porogens to provide porous films having dielectric constants of 1.9.

Figure 9:
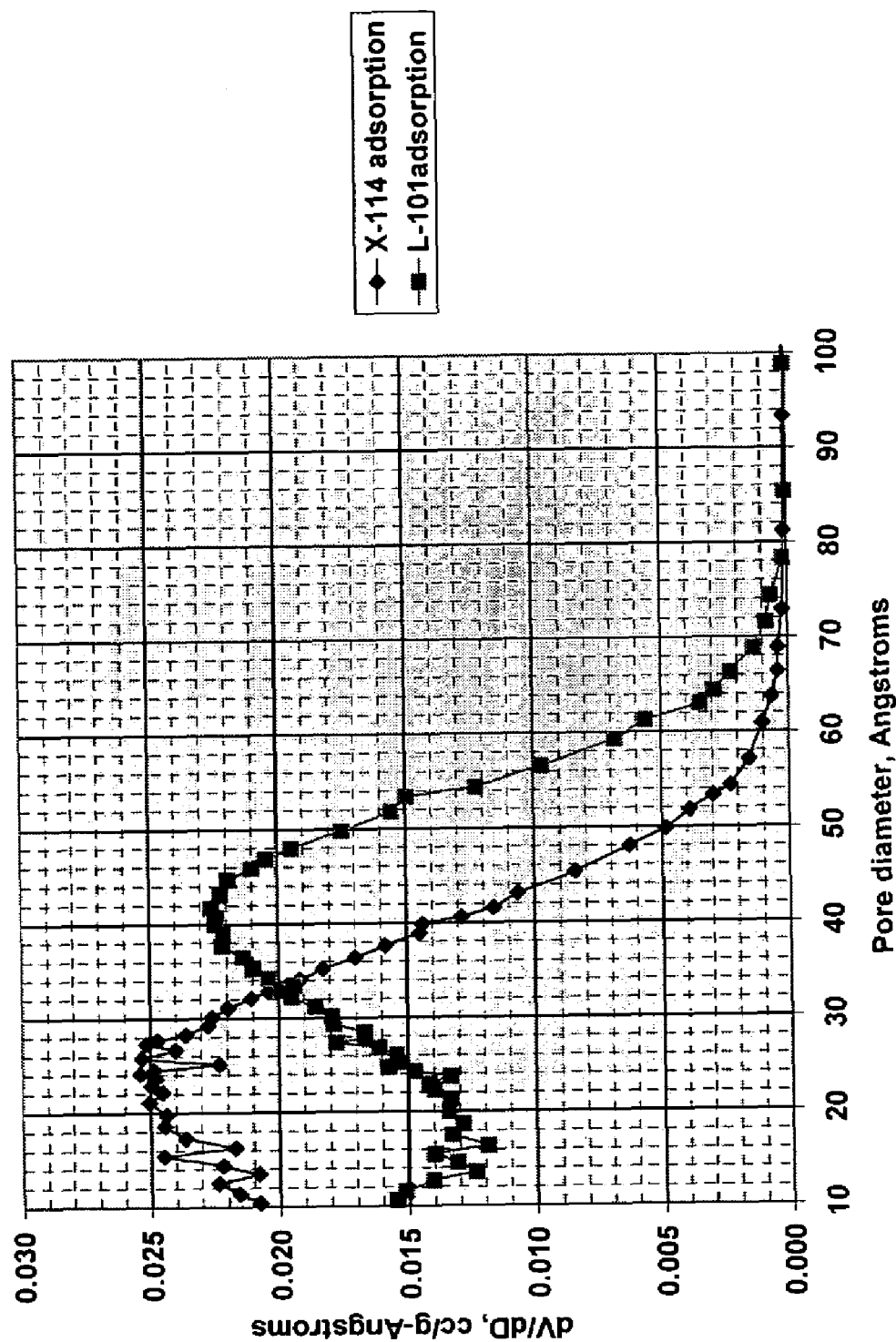

FIG. 9 provides a plot of dV/dD vs. pore diameter derived from ASAP BJH calculations (BJH parameters: 10-3000 Å, F=0, default ASAP Halsey) using the adsorption branch of the isotherm for $N_2$ at 77 K on low κ films prepared using Triton X-114 and Pluronic L-101 surfactants as porogens to provide porous films having dielectric constants of 1.9.

Figure 10:
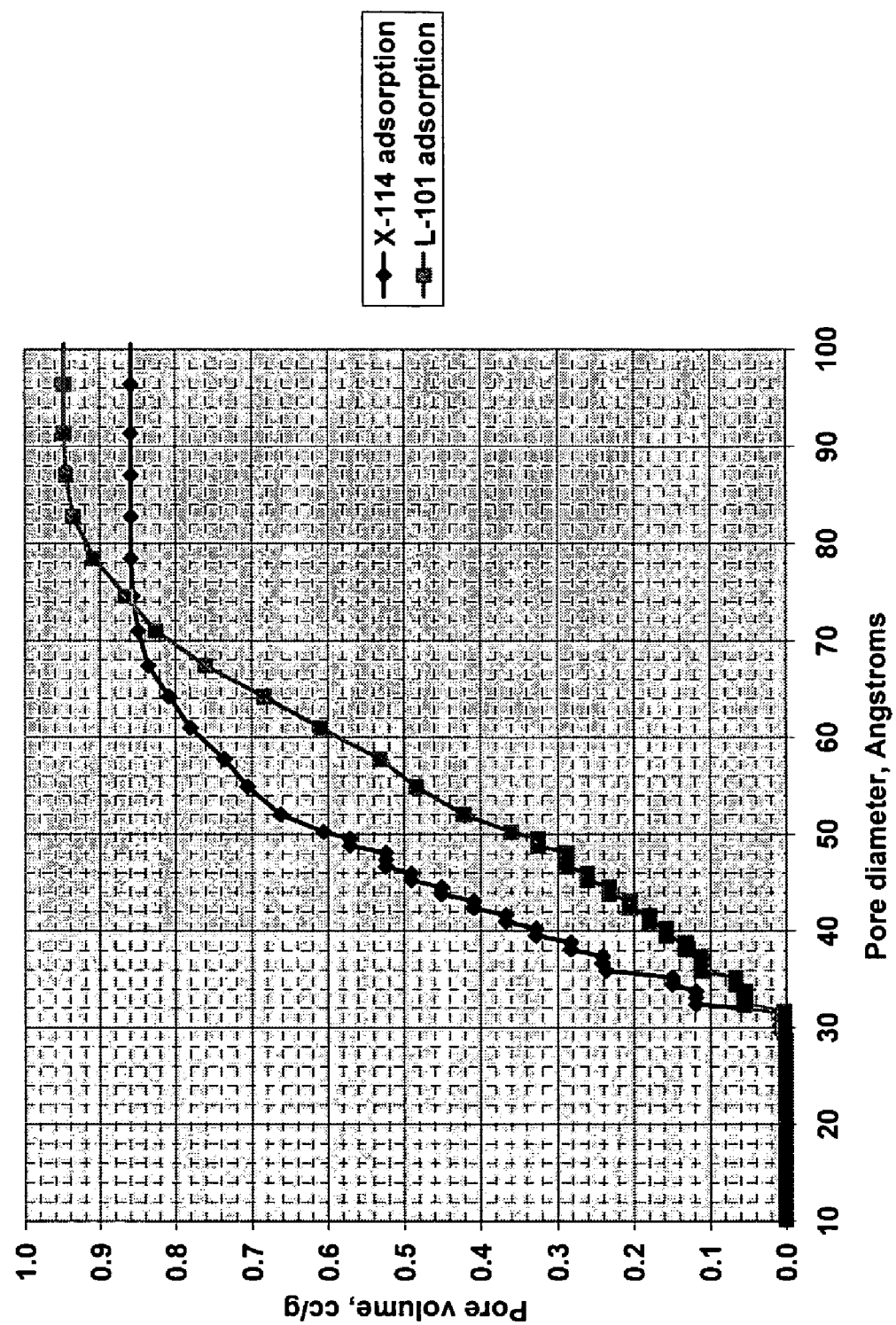

FIG. 10 provides a plot of cumulative pore volume vs. pore diameter derived from ASAP DFT calculations (DFT parameters: regularization=0, $P/P_0<0.95$) using the adsorption branch of the isotherm for $N_2$ at 77 K on low κ films prepared using Triton X-114 and Pluronic L-101 surfactants as porogens to provide porous films having dielectric constants of 1.9.

Figure 11:
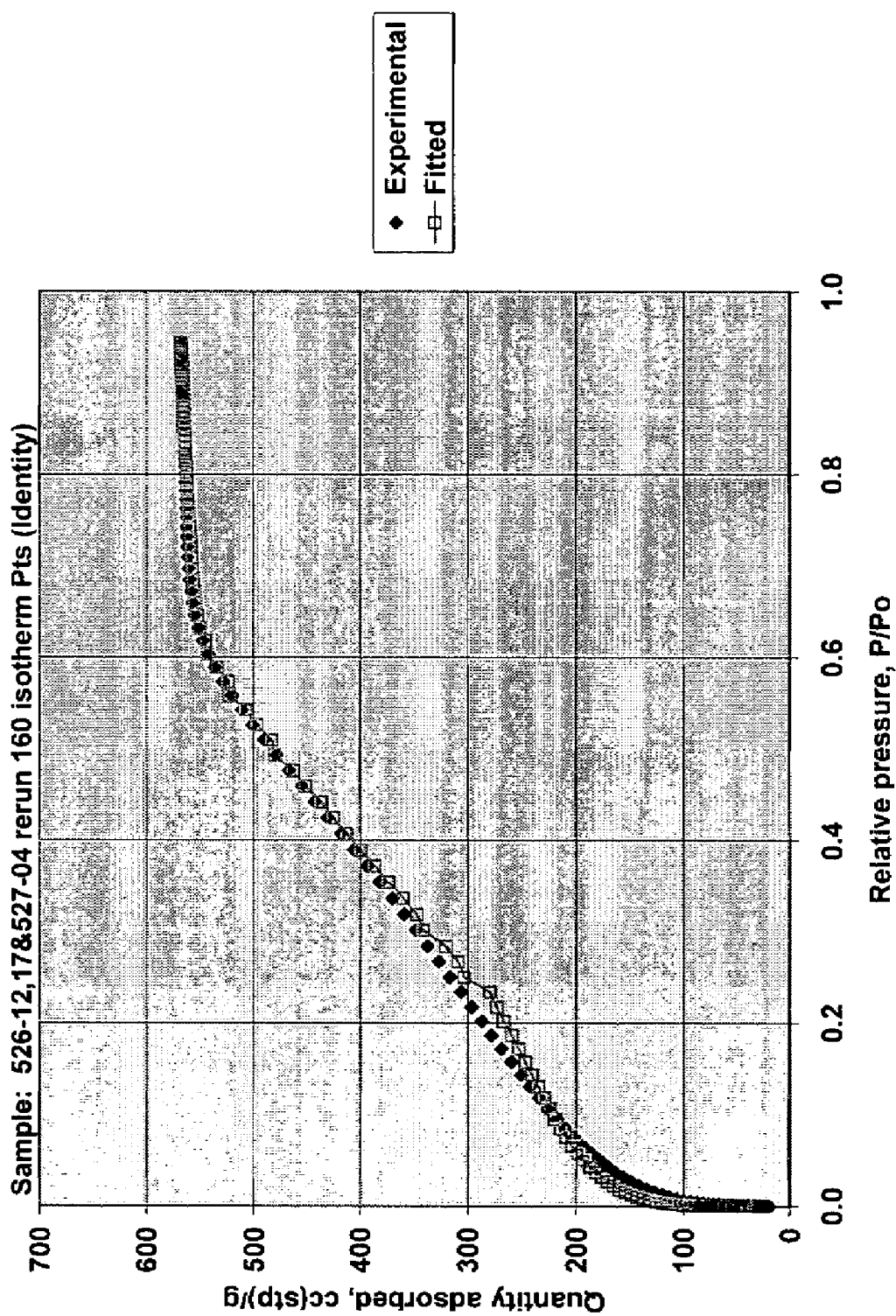

FIG. 11 provides a comparison of interpolated experimental data points for the adsorption branch of the $N_2$ isotherm at 77 K on 1.9 κ films prepared using Triton X-114 surfactant as the porogen to the fitted data points from the ASAP DFT calculations (DFT parameters: regularization=0, $P/P_0<0.95$).

Figure 12:
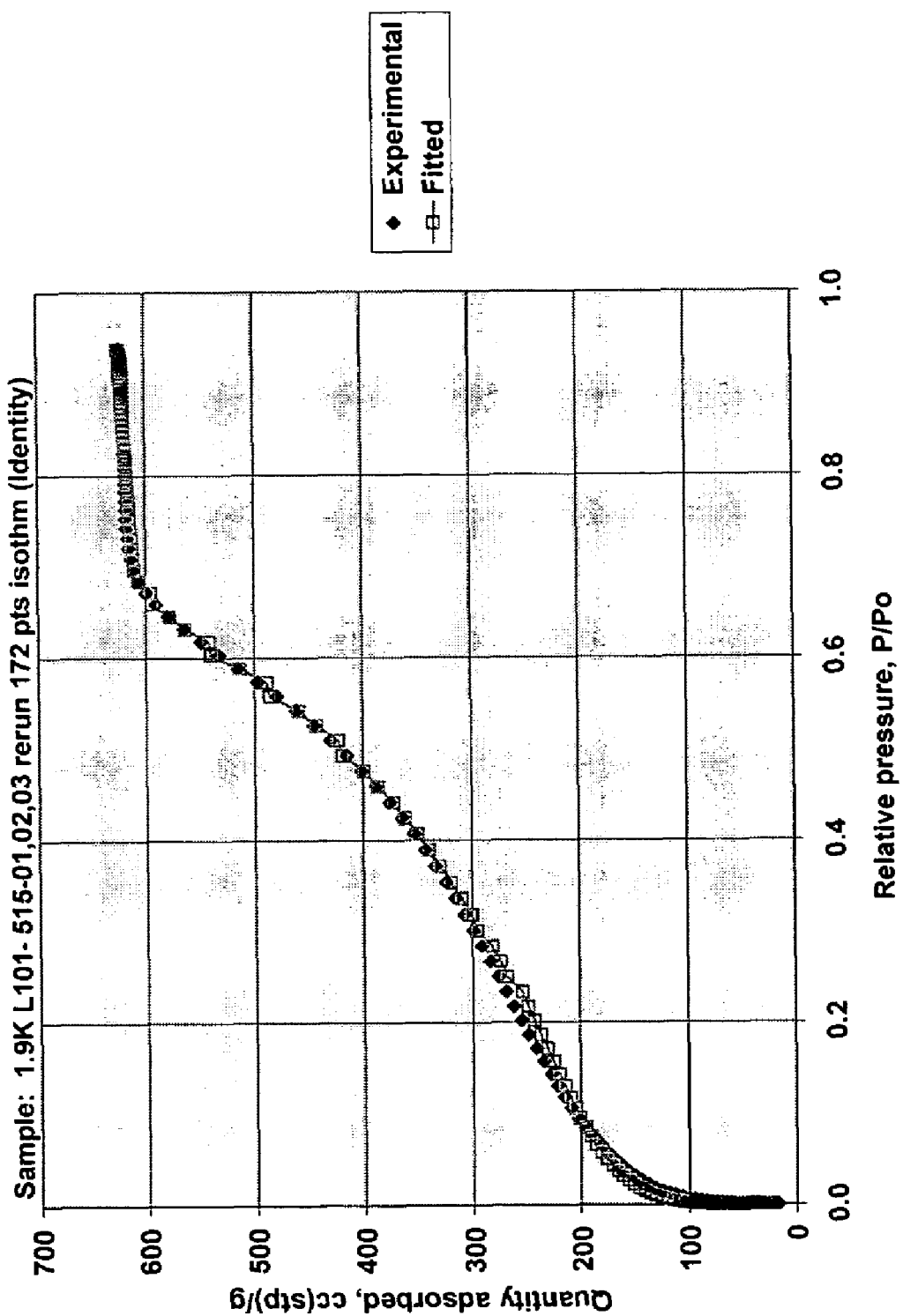

FIG. 12 provides a comparison of interpolated experimental data points for the adsorption branch of the $N_2$ isotherm at 77 K on 1.9 κ films prepared using Pluronic L-101 surfactant as the porogen to the fitted data points from the ASAP DFT calculations (DFT parameters: regularization=0, $P/P_0<0.95$).

DETAILED DESCRIPTION OF THE INVENTION

A method to characterize the porosity in films, such as low dielectric constant porous films, while still on the wafer using adsorption is described herein. The method described herein may be used to determine the pore size distribution and the presence or absence of killer pores within at least a portion of a porous film that is deposited upon a substrate. A maximum pore diameter may be determined from the pore size distribution. In one particular embodiment, a maximum pore diameter can be defined by the slope in the plot of cumulative pore volume vs. pore diameter. In this embodiment, the presence or absence of killer pores can be determined by comparing the maximum pore diameter to the killer pore diameter that has been established for that application or a reference pore diameter. The method described herein may allow for the quantification of the maximum pore diameter without complications from apparent porosity due to condensation of the adsorbate in the interstices between particles. In this regard, the condensation of the adsorbate in the interstices may result in a sharp upturn in the isotherm at high $P/P_0$ that cannot be distinguished from the presence of large pores in the pore size distribution calculations. As a result, the presence (or absence) of killer pores cannot be easily determined.

Figure 1:
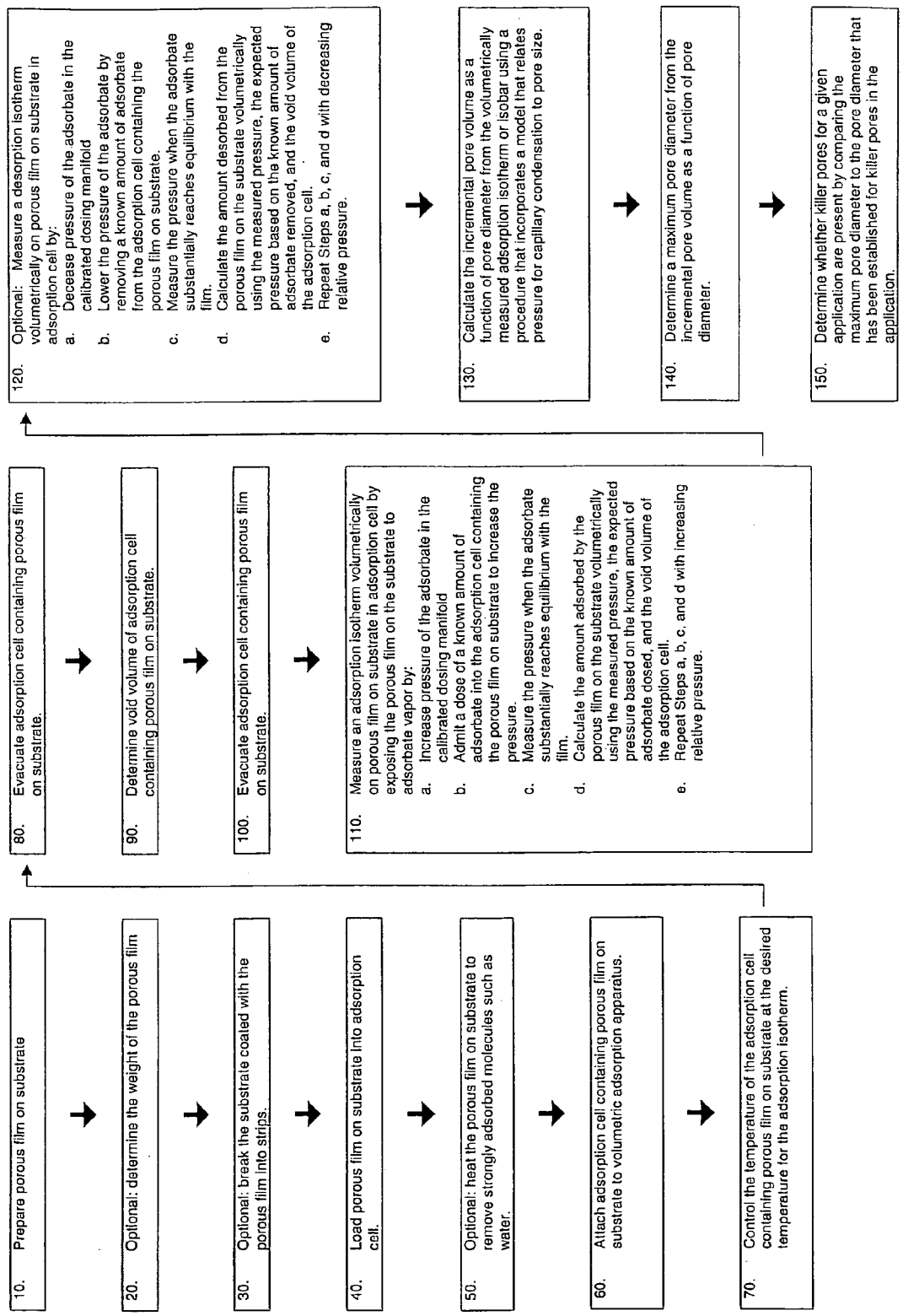
FIG. 1 provides a flow diagram for one embodiment of the method of the present invention.

FIG. 1 provides a flow diagram for one embodiment of the method of the present invention. In this embodiment, a porous film that is deposited upon a substrate is exposed to an adsorbate at a temperature and a pressure sufficient to result in capillary condensation of the adsorbate in the pores of the film. The amount adsorbed is measured volumetrically. In one embodiment, the amount adsorbed can be determined for different pressures at constant temperature (adsorption isotherm). In another embodiment, the amount adsorbed can be determined for different temperatures at constant pressure (adsorption isobar). The pore size distribution for the film is calculated from the amount adsorbed using an algorithm that incorporates a theoretical model for capillary condensation. In one embodiment, the algorithm, such as, for example, that proposed by Barrett, Joyner, and Halenda (BJH), in the reference "The Determination of Pore Volume and Area Distributions in Porous Substances. I. Computations from Nitrogen Isotherms", J. Am. Chem. Soc., Vol. 73, pp. 373-380 (1951), which incorporates classical macroscopic models for capillary condensation such as the Kelvin model, may be used. These techniques may define an average pore size or the pore size corresponding to the peak in the differential volume distribution (dV/dD) plot.

Figure 2:
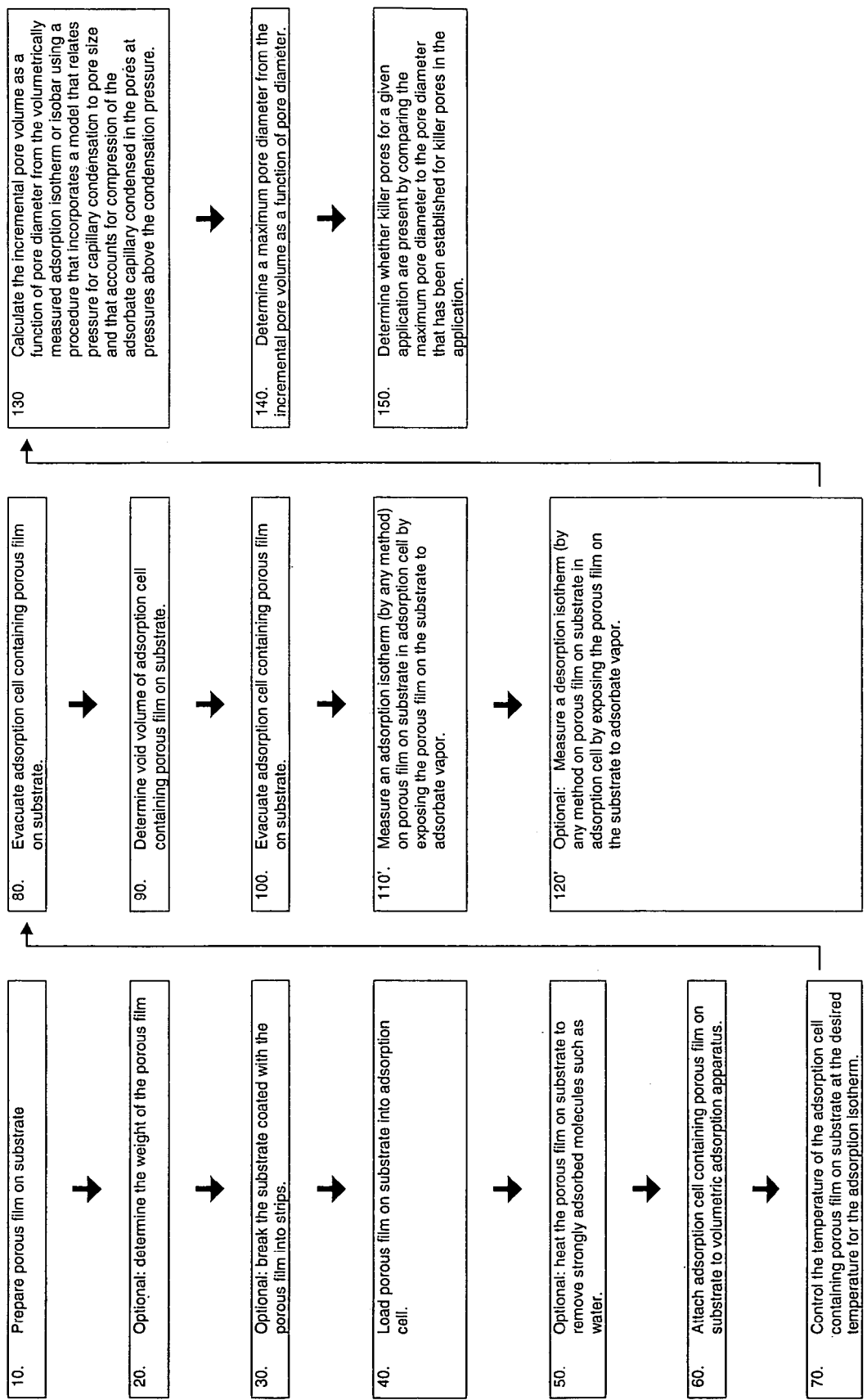
FIG. 2 provides a flow diagram for another embodiment of the method of the present invention.

FIG. 2 provides a flow diagram for another embodiment of the method of the present invention. In this embodiment, the pore size distribution is calculated from the adsorption isotherm or adsorption isobar using a procedure that incorporates a model for capillary condensation that accounts for compression of the adsorbate capillary condensed in the pores. In this embodiment, the procedure used, for example, is the Generalized Adsorption Isotherm (GAI) equation that incorporates microscopic models for capillary condensation, such as Density Functional Theory (DFT). The use of DFT allows quantification of the maximum pore diameter without complications from apparent porosity from the gradual slope in the isotherm at high $P/P_0$. The gradual slope in the isotherm at high $P/P_0$ from compression cannot be distinguished from the presence of large pores by the BJH/Kelvin model for calculating the pore size distribution. The DFT model can be used with adsorption data for the porous film on the substrate at temperature and pressure conditions that result in capillary condensation of the adsorbate in the pores of the film measured by any technique, not just measured volumetrically.

Figure 3:
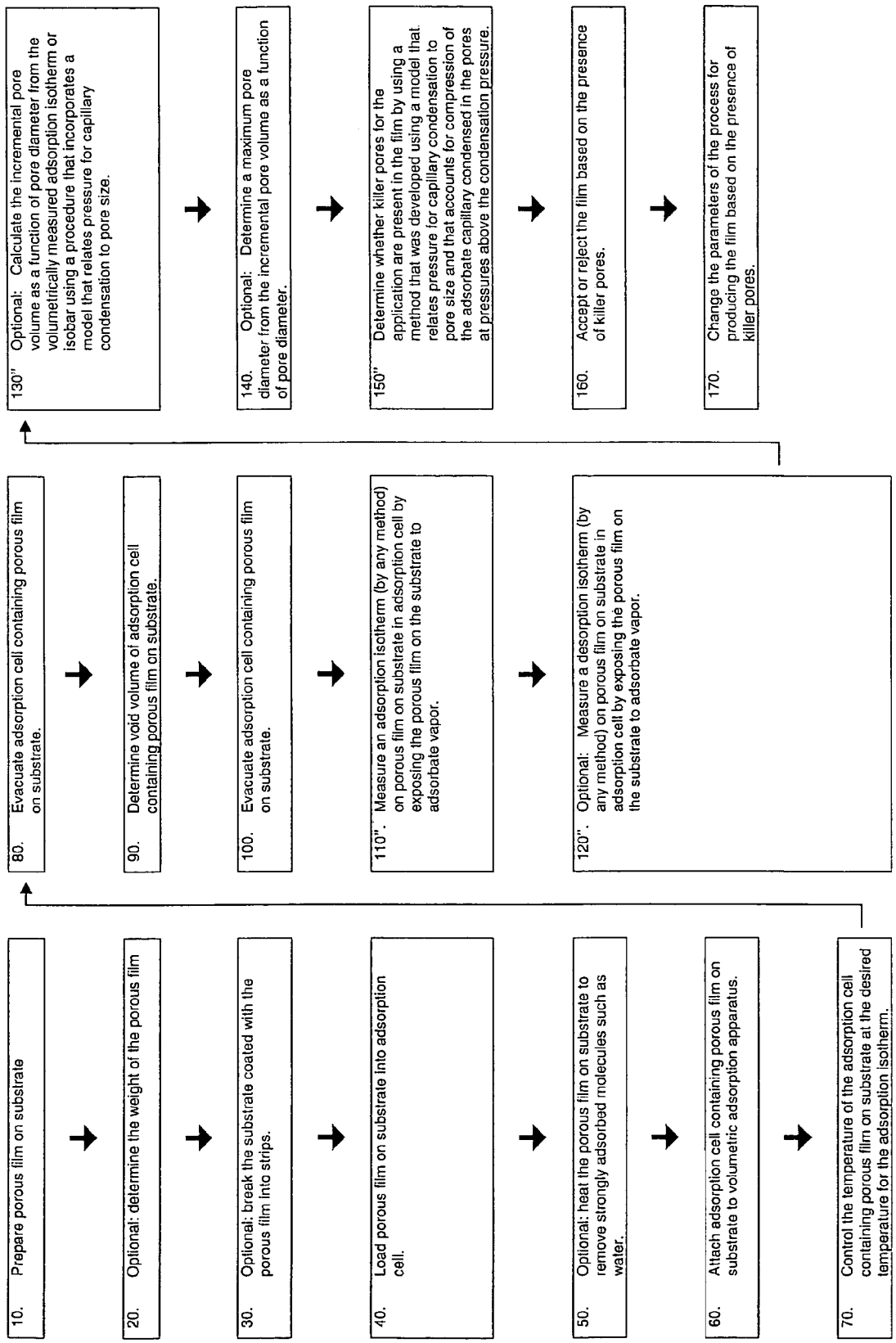
FIG. 3 provides a flow diagram for a further embodiment of the method of the present invention.

FIG. 3 provides a flow diagram for a further embodiment of the method of the present invention wherein the porosity characterization is used as part of a quality control test and/or process control tool in a process for fabricating porous films on substrates. In these embodiments, a complete isotherm or isobar may not be measured, but only a limited number of adsorption data points might be measured for the porous film on a substrate at temperature and pressure conditions that result in capillary condensation of the adsorbate in the pores of the film. In this case, the step to determine whether killer pores for the application are present in the film uses a method that was developed using a model that relates pressure for capillary condensation to pore size and that accounts for compression of the adsorbate capillary condensed in the pores at pressures above the condensation pressure. Based on the presence of killer pores, the film can be accepted or rejected, and/or the parameters of the process for producing the film can be modified.

The pore size distribution and/or determination of the presence or absence of killer pores is performed on at least a portion of a porous film that is deposited upon a substrate. Examples of suitable configurations for the substrate include, but are not limited to, a plate, wafer, wire mesh, formed monolith, formed catalyst particle, etc. The substrate is substantially non-porous or, alternatively it could have large macroscopic pores like a monolith or a ceramic catalyst support. Examples of suitable materials for the substrate include, but are not limited to, metal, metalloid, ceramic, organic, and combinations thereof. In one particular embodiment, the substrate is a single crystal, such as a single crystal silicon wafer. In these embodiments, the method described herein may be beneficial if the size of the substrate on which the film is deposited is greater than about 1 inch in at least two of its dimensions or greater than about 2 inches in at least two of its dimensions. Table I provides non-limiting examples of typical thicknesses and other dimensions of silicon wafers used in the semiconductor industry.

TABLE I

Typical Thickness of Silicon Wafers Used in the Semiconductor Industry

| Diameter (mm) | Diameter (in) | Thickness (mm) |
| --- | --- | --- |
| 50 | 2 | 0.25-0.30 |
| 100 | 4 | 0.50-0.55 |
| 200 | 8 | 0.70-0.75 |
| 300 | 12 | 0.75-0.80 |

In step 10, a porous film is deposited upon a substrate. The porous film can be deposited onto the substrate by a variety of manufacturing process such as but not limited to, spin-on, CVD (including PECVD), dip, PECVD, spray, transport polymerization, non-contact induced spreading forces. The film composition can be organic, inorganic, hybrid, etc. In one embodiment, the film is silica-based. The film is porous. In certain embodiments, the porous film may be "open-pore" meaning that at least a portion of the porosity may be accessible to the gas phase. In one embodiment, the porosity is formed in the film through the introduction of a porogen that is at least partially removed during a drying, curing, annealing, or other processing step. A "porogen" is a reagent that is used to generate void volume within the resultant film. Suitable porogens for use in the porous films disclosed herein include labile organic groups, high boiling point solvents, decomposable polymers, surfactants, dendrimers, hyperbranched polymers, polyoxyalkylene compounds, organic compounds, or combinations thereof. Further examples of porogens may be found in U.S. patent application Ser. No. 10/150,798, which is incorporated herein by reference in its entirety. The film forming process may include heating steps called by various names such as drying, calcining, curing, etc. Likewise, a variety of processes can be used for curing these materials to decompose and/or remove volatile components and substantially crosslink the films such as heating, treating the materials with plasmas, electron beams, UV radiation, etc. The porogen may be removed during the curing step. The porous film may or may not have order. The porous film may or may not be crystalline.

In one embodiment, the size of the pores contained within the porous film is mesoporous, i.e., having an average pore diameter that ranges from 20 to 500 Å. However, in other embodiments, the pores may have an average pore diameter that is less than 20 Å or "microporous" or greater than 500 Å in diameter or "macroporous". The porous films may be a combination of micro-, meso-, and macropores. However, in certain analytical methods, it may be difficult to characterize macropores because the relative pressures for condensation in macropores are close to unity. If DFT is used, microporosity can be characterized. In certain embodiments, the film is an open pore film exhibiting open porosity greater than about 0.2 cc/g. In one embodiment, the fraction of porosity in the film is at least about 40% (based on 2.7 κ film). One of the reasons for the unexpected result of being able to measure the uptake volumetrically is that the films have a large void fraction. This can be defined by the surface area. In one embodiment, the total surface area in the adsorption cell is greater than about 14 m$^2$ (based on 2.7 κ film). The film thickness is less than 1 mm. One embodiment is to prepare films thicker than would be used for the application in order to obtain more mass of the material and consequently a larger adsorption volume in the adsorption cell. For example, films 1.5 microns (μm) in thickness would be prepared with the same formulation as the 0.5 μm film used in the application, but modifying the process parameters or formulation, for example with less solvent, to obtain a thicker film. This assumes the pore size distribution of the thicker film will be the same as the pore size distribution of the thinner film.

In optional step 20, the weight of the film is determined by weighing the substrate on a high sensitivity balance before and after depositing the coating. In these embodiments, the adsorption uptake may be reported in cubic centimeters ("cc") at standard temperature and pressure ("stp"), or cc (stp)/weight of film. In alternative embodiments, the thickness of the film can be determined by any of a number of techniques and the adsorption uptake may be reported in cc (stp)/volume of film.

In optional step 30, one or more single substrates such as, for example, a silicon wafer having a porous film deposited thereupon, can be broken into strips that are small enough to fit into a standard large glass or quartz adsorption cell. This may allow for commercially available volumetric adsorption equipment to be used to measure the adsorption/desorption isotherm, for example, using nitrogen ($N_2$) at a temperature of 77 K. In embodiments wherein the substrate is a single crystal substrate, the substrate can be broken into strips along lattice planes without damaging the relatively fragile film, i.e., films having an elastic modulus that ranges from 1 to 6 GPa. In one embodiment of the invention, relatively thick films (i.e., having a thickness of about 1 to 1.5 μm or greater) are deposited upon silicon wafers, the wafers are broken into thin strips, and the strips from several wafers are packed into a slightly larger than normal adsorption cell. In one particular embodiment, breaking the substrate into strips may be beneficial if the size of the substrate having the porous film deposited thereupon is greater than about 1 inch in at least two of its dimensions or greater than about 2 inches in at least two of its dimensions. In this embodiment, the resultant strips may be less than about 2 inches in at least two of their dimensions. In other embodiments, such as where the method described herein is used as a quality control tool, breaking the substrate into strips may not be desirable.

In step 40, one or more intact substrates having the porous film deposited thereupon and/or the strips of one or more of the substrates having the porous film deposited thereupon are loaded into a vessel for analysis such as, for example, an adsorption cell. The adsorption cell may be, for example, a standard large glass or quartz adsorption cell. The adsorption cell may exhibit at least one of the following characteristics: has low void volume or free space; provides a good seal under vacuum; and has sufficient structural integrity so that the void volume does not change when the adsorption cell is evacuated. The film/substrate broken into strips can be loaded into the cell. The strips from one or more substrate having the porous film deposited thereupon can be loaded into the cell. Alternatively, the adsorption cell may hold the substrate having the porous film deposited thereupon without breaking into strips. More than one wafer having the porous film deposited thereupon could be loaded into the cell to increase the sensitivity of the measurement. In certain embodiments, a filler tube can be added to the adsorption cell to reduce the free space. In other embodiments, an apparatus may be added to the adsorption cell such as an Isothermal Jacket™ tube provided by Micromeritics that acts as a wicking tube to keep the sample cell isothermal as the level of liquid $N_2$ falls during the experiment.

In optional step 50, one or more substrates having the porous film deposited thereupon and/or the strips of the substrate having the porous film deposited thereupon may be heated to remove strongly adsorbed molecules such as water. The substrate or strip of substrate having the porous film deposited thereupon can be heated at various times before exposure to the adsorbate. For example, the substrate having the porous film deposited thereupon could be heated and transferred to the adsorption cell without exposure to ambient air; the substrate having the porous film deposited thereupon could be broken into strips in a glove box and could be heated in the adsorption cell in a separate apparatus; the substrate having the porous film deposited thereupon could be heated in the adsorption cell after being attached to the adsorption apparatus; and combinations thereof. In these embodiments, the temperature that the heating step is performed at is high enough to desorb the strongly adsorbed molecules but not so high as to damage the film. The desorbed molecules could be removed by vacuum, by inert gas flow, or other means. In other embodiments, however, heating may not be required. For example, if the porogen is completely removed during the preparation of the film and/or the film does not adsorb molecules from the environment in which it is handled that cannot be removed by evacuation at ambient temperature, the heating step may not be necessary.

Figure 4:
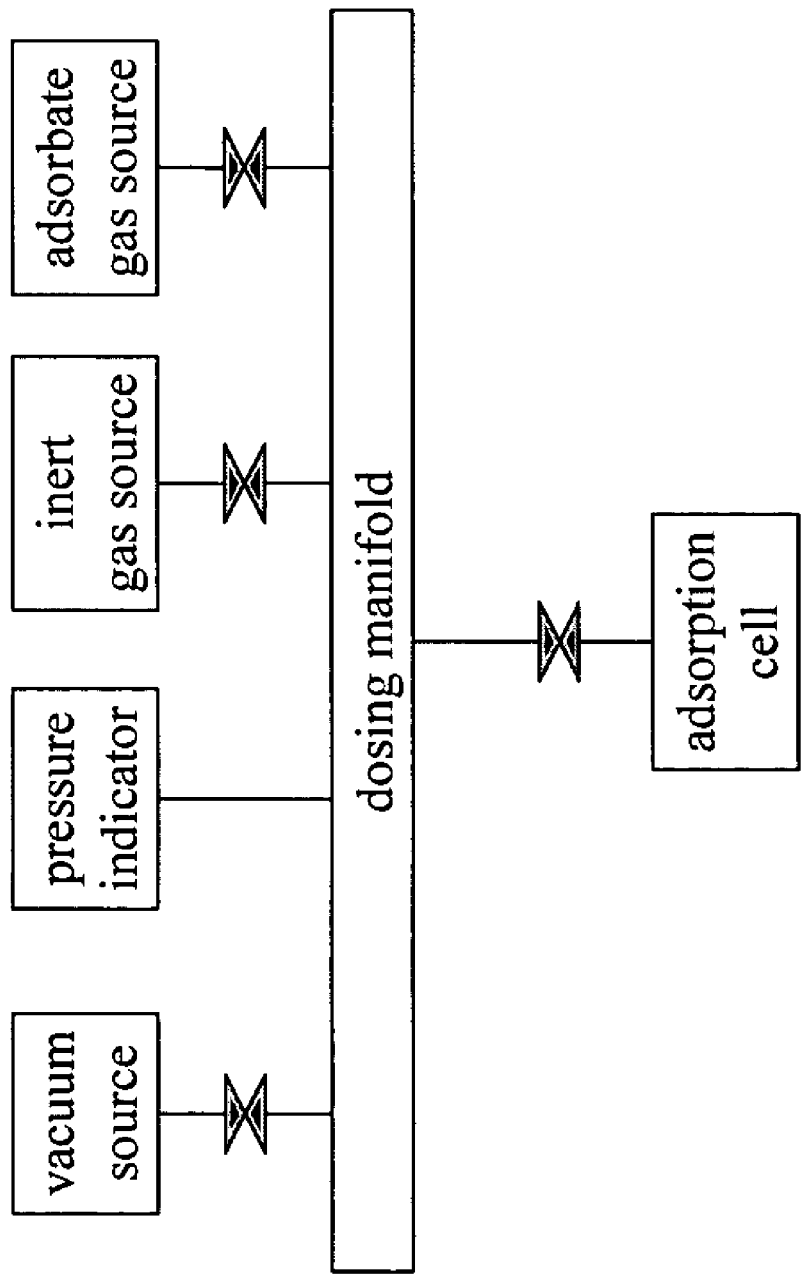
FIG. 4 provides an example of a volumetric adsorption apparatus that may be used with the method of the present invention.

After the adsorption cell is loaded with one or more substrates having the porous film deposited thereupon or one or more strips of substrate having the porous film deposited thereupon, in step 60 the adsorption cell may be attached to a volumetric adsorption apparatus. The volumetric adsorption apparatus may comprise, for example, a calibrated dosing manifold, a source of an inert gas for determining the void volume or free space of the adsorption cell, a source of the condensable adsorbate gas or vapor, and a means of evacuating the system. A schematic for a typical volumetric adsorption apparatus is provided in FIG. 4. Some examples of commercially available volumetric adsorption equipment include, but are not limited to, the Micromeritics Accelerated Surface Area and Porosimetry (ASAP) System and the Quantachrome Autosorb. In embodiments wherein the method is used as a quality control technique, the volumetric adsorption apparatus may differ. For example, the inert gas source might not be required if the void volume is always the same.

In step 70, the temperature of the adsorption cell having the substrate(s) or strip(s) of substrate having the porous film deposited thereupon contained therein is controlled for the adsorption isotherm. The temperature is below the critical temperature of the adsorbate in order to observe capillary condensation in the pores of the film. In certain embodiments, the temperature is at or below the boiling point of the adsorbate for then the maximum pressure in the adsorption isotherm will be one atmosphere. In embodiments wherein the adsorbate is nitrogen ($N_2$) or the adsorbate is toluene, the temperature is 77 K and room temperature, e.g., 23° C., respectively. In certain embodiments, the temperature can be controlled by a device such as a dewar, which can hold liquid nitrogen at 77 K, an air or liquid constant temperature bath, a temperature controlled room, or other means. In an embodiment wherein the adsorbate is liquid $N_2$, an Isothermal Jacket™ that acts as a wicking tube can be used to keep the sample cell isothermal as the level of liquid $N_2$ falls during the experiment.

In step 80, the adsorption cell having the substrate(s) or strip(s) having the porous film deposited thereupon to be analyzed is evacuated using, for example, one or more vacuum pumps, zeolites cooled to 77 K, or other means. The quality of the vacuum required depends on the pressure range of interest for capillary condensation in the pore size of the film of interest for the adsorbate at the temperature of interest.

In step 90, the void volume of adsorption cell having the substrate(s) or strip(s) having the porous film deposited thereupon contained therein is determined using one of more methods such as, for example, Webb and Orr, *Analytical Methods in Fine Particle Technology*, which is incorporated herein by reference in its entirety. In the apparatus shown in FIG. 4, a valve separates the dosing manifold from the adsorption sample cell. The void volume is that volume contained within the adsorption cell up to that valve and should be known in order to calculate the amount of gas in that void volume. In some embodiments, the void volume may be determined for a representative sample and/or for the adsorption cell and then adjusted for the sample. The void volume determination can be achieved in a variety of ways. In one embodiment, the void volume may be measured immediately prior to the sorption analysis. A non-adsorbing gas, such as helium, is expanded or dosed from a known, calibrated volume (such as the dosing manifold shown in FIG. 4) into the adsorption cell containing the sample. The principles of the gas laws, primarily Boyle's Law, are applied. In this embodiment, the void volume determination is performed at ambient temperature using that portion of the cell containing the sample at the analysis temperature. In an alternative embodiment, the void volume is not calculated directly, but the amount of analysis gas, the adsorptive that is transferred from the manifold to an empty cell, is measured as a function of pressure, under the same conditions of temperature as the subsequent analysis, and can be done at one or more discrete pressures such as that disclosed in U.S. Pat. No. 6,387,704. The void volume can be determined at room temperature and after controlling the adsorption cell at the temperature of the isotherm.

After the void volume is determined, in step 100, the adsorptive cell may be evacuated.

In step 110, the adsorption isotherm of the film deposited on the substrate(s) or strip(s) of substrate may be measured volumetrically in the adsorptive cell by exposing the substrate(s) or strip(s) having the porous film deposited thereupon contained therein to an adsorbate gas or vapor. The adsorption isotherm may be measured for the entire film on the substrate or strip of substrate rather than a portion of the film on the substrate or strip. In this step, the conditions for the introduction of the adsorbate gas or vapor, the temperature, the pressure, etc. of the adsorption cell should be sufficient to result in volume filling and/or capillary condensation of the adsorbate in the pores of the film. The adsorbate can be any adsorbate that can capillary condense in at least a portion of the pores of the film at a certain temperature, such as, for example, $N_2$ in embodiments wherein the temperature is 77 K, or toluene wherein the temperature is room temperature. In certain embodiments, the adsorbate is a non-polar gas without a permanent dipole. Further examples of adsorbates include, but are not limited to, nitrogen, toluene, argon, krypton, oxygen, neopentane, and $CF_4$. The temperature for the isotherm may be at or below the critical temperature of the adsorbate.

In some embodiments, a temperature of 77 K and a $N_2$ adsorbate may be used because adsorption equipment is commercially available for $N_2$ adsorption at 77 K, and procedures/models such as BJH/Kelvin and GAI/DFT to convert the adsorption isotherm to a pore size distribution are worked out for many scenarios for $N_2$ at 77 K. Software is also available for controlling adsorption/desorption isotherms in commercially available volumetric adsorption equipment such as, but not limited to, Micromeritics ASAP software or Quantachrome Autosorb software. Further, there is an ASTM Standard Test Method (D-4222-98) for Determination of Nitrogen Adsorption and Desorption Isotherms of catalysts by Static Volumetric Measurements written for $N_2$ adsorption at 77 K. In another embodiment, argon is the adsorbate and the adsorption is conducted at 87 K. In a still further embodiment, toluene is used as the adsorbate because the adsorption cell does not need to be cooled to 77 K but can be controlled at room temperature. The pressure range is such that results in capillary condensation of the adsorbate in the pores of interest at the isotherm temperature. For embodiments wherein the adsorbate is $N_2$ and the temperature is 77 K, the pressure may range from about $1 \times 10^{-5}$ to approximately 1 atmosphere (atm). In embodiments wherein the porous film deposited on the substrate(s) is a silica-based film that is used as an inter-level dielectric, the pressure range for a $N_2$ adsorbate at a temperature of 77 K may be from about 0.1 to about 1 atm or from 0.5 to 1 atm. The number of data points that is collected in the isotherm should be sufficient to fully characterize the shape of the isotherm in the regions of interest. In one embodiment, thirty points evenly spread over the isotherm may be considered enough to adequately define the isotherm. If the isotherm exhibits sharp steps, more points through the region of the step might be desirable. In other embodiments, a relatively few high relative pressure data points might be all that is required if the method is used as a quality control tool for low κ film fabrication to detect killer pores. If the adsorption isotherm shows a type H2 hysteresis loop in the classification of hysteresis loops as recommended by the International Union of Pure and Applied Chemistry (IUPAC) then the adsorption branch of the isotherm may be used; if the isotherm shows a type H1 hysteresis loop then either the adsorption branch or the desorption branch of the isotherm may be used.

The volumetric procedure for determining the adsorption isotherm may comprise, for example, the following steps:
  (a) Increase pressure of the adsorbate in the calibrated dosing manifold;
  (b) Admit a dose of a known amount of adsorbate into the adsorption cell containing the porous film on substrate to increase the pressure;
  (c) Measure the pressure when the adsorbate substantially reaches equilibrium with the film;
  (d) Calculate the amount adsorbed by the pores within the film on the substrate volumetrically using the measured pressure, the expected pressure based on the known amount of adsorbate dosed, and the void volume of the adsorption cell; and
  Repeat steps (a), (b), (c) and (d) with increasing relative pressure.

In optional step 120, a desorption isotherm may be measured volumetrically on the porous film deposited on the substrate. In some embodiments, the adsorption branch of the isotherm may be used to calculate the pore size distribution whereas in other embodiments the desorption branch may be used. For example, the adsorption branch of the isotherm may be appropriate for a Type IV isotherm as in the Brunauer classification with a type H2 hysteresis loop that indicates the presence of ink-bottle pores. Alternatively, either the adsorption or the desorption branch of the isotherm may be appropriate for a Type H1 hysteresis loop or no hysteresis provided that the appropriate model for capillary condensation (pore filling) is used. In embodiments wherein the desorption isotherm is used, the volumetric procedure for determining the desorption isotherm comprises:
  (a) Decrease pressure of the adsorbate in the calibrated dosing manifold;
  (b) Lower the pressure of the adsorbate by removing a known amount of adsorbate from the adsorption cell containing the porous film on substrate;
  (c) Measure the pressure when the adsorbate substantially reaches equilibrium with the film;
  (d) Calculate the amount desorbed from the porous film on the substrate volumetrically using the measured pressure, the expected pressure based on the known amount of adsorbate removed, and the void volume of the adsorption cell; and
  Repeat steps (a), (b), (c), and (d) with decreasing relative pressure.

In embodiments wherein the adsorption isotherm shows a type H1 hysteresis loop, then either the adsorption branch or the desorption branch of the isotherm could be used.

In optional step 130, the incremental pore volume may be calculated as a function of pore diameter from the volumetrically measured adsorption isotherm or isobar using a mathematical procedure or algorithm that incorporates a model that relates pressure for capillary condensation to pore size. A number of procedures may be used for calculating the incremental pore volume as a function of pore diameter from the adsorption isotherm. Examples of suitable procedures include Barrett, Joyner, and Halenda (BJH) and the Generalized Adsorption Isotherm (GAI) equation. The BJH procedure is typically used with the Kelvin model for capillary condensation, and the GAI equation is typically used with DFT. In certain embodiments, however, the GAI equation has also been applied with classical models such as the Kelvin equation. There have been a number of modifications to the original BJH procedure, some are commercially available, for instance in Quantachrome Autosorb or Micromeritics ASAP software. The input parameters for the calculations of pore size distribution from the isotherm depend upon the type of the porosity (e.g., cylindrical pores vs. a network of pores), the energetics of the surface (hydrophobic vs. hydrophilic), and a variety of other factors.

Likewise, a number of theoretical models are available that relate pressure for capillary condensation (pore filling) to pore size such as Kelvin, Kelvin-Cohan, empirically modified Kelvin by Jaroniec, DFT, or other models. These models may depend on the pore geometry. A cylindrical pore shape is often appropriate for the model used to relate pressure for capillary condensation to pore size; other pore geometries such as spheres, slits, etc., may be appropriate. The model can incorporate the multilayer thickness of the adsorbate on the walls of the pores. A reference isotherm appropriate for the surface energy of the sample can be used. For some silica-based low κ type films, a more hydrophobic type reference isotherm than hydroxylated silica may be more appropriate. However, for many applications this may not make a large impact if the pressure that corresponds to capillary condensation in the pores gives a multilayer thickness greater than a monolayer.

Various models and procedures that can be used to calculate the pore size distribution from the adsorption isotherm are described below. Nitrogen ($N_2$) is used as an example of the adsorbate gas at 77 K, but the models and procedures may be applicable to other adsorbates and temperatures. Exposure of mesoporous materials to increasingly higher pressures of $N_2$ vapor at 77 K results in capillary condensation of $N_2$ in the pores of the material. The classical model for adsorption in cylindrical pores views the adsorbed phase as consisting of two components, the core and the film adsorbed on the pore wall. The core radius is modeled by the Kelvin equation, and the adsorbed film is modeled by a multilayer (statistical) film thickness equation. The pore radius ($r_p$) is determined from the core radius ($r_c$) and the film thickness (t) as shown in Equation (1).

$$r_p = r_c + t \tag{1}$$

In principle, the processes of capillary condensation and evaporation should occur reversibly in a closed tapering pore. At low relative pressures the concentration of adsorbed molecules in the narrow end of the pore (micropore region) is enhanced compared to adsorption on the rest of the surface. As the pressure is increased, at some value of $P/P_0$, a meniscus begins to form; as $P/P_0$ increases further, the meniscus moves steadily up toward the pore entrance. Evaporation proceeds in the reverse direction with the same elemental steps. The meniscus for evaporation from a closed tapering pore is the same shape as the meniscus for condensation.

The Kelvin equation for the core radius is based on the relationship between the vapor pressure and the mean radius of curvature of the hemispherical meniscus of liquid $N_2$ condensed in the pore according to the following Equation (2):

$$r_m = \frac{-2\gamma v \cos\theta}{RT \ln(P/P_0)} \tag{2}$$

In Equation (2), each variable represents the following: $r_c$=mean radius of curvature of the liquid meniscus of the pore core; $\gamma$=liquid surface tension; $v$=molar volume of the condensed adsorbate; $\theta$=contact angle between the solid and condensed phase; R=ideal gas constant; T=temperature; and P=critical condensation pressure. The contact angle between the solid and the condensed $N_2$ is typically assumed to be zero which would allow cos $\theta$=1.

In certain embodiments, the adsorption/desorption process is not reversible which results in hysteresis in the adsorption/desorption isotherm. There are a number of possible reasons for hysteresis, one of them being open cylindrical pores. Cohan more fully defined the core radius for open cylindrical pores as a mean radius. The Kelvin-Cohan Equation, or Equation (3) provides the mean radius of curvature of the pore core:

$$r_m = \frac{-2\gamma v \cos\theta}{RT \ln(P/P_0)} \tag{3}$$

Figure 5:
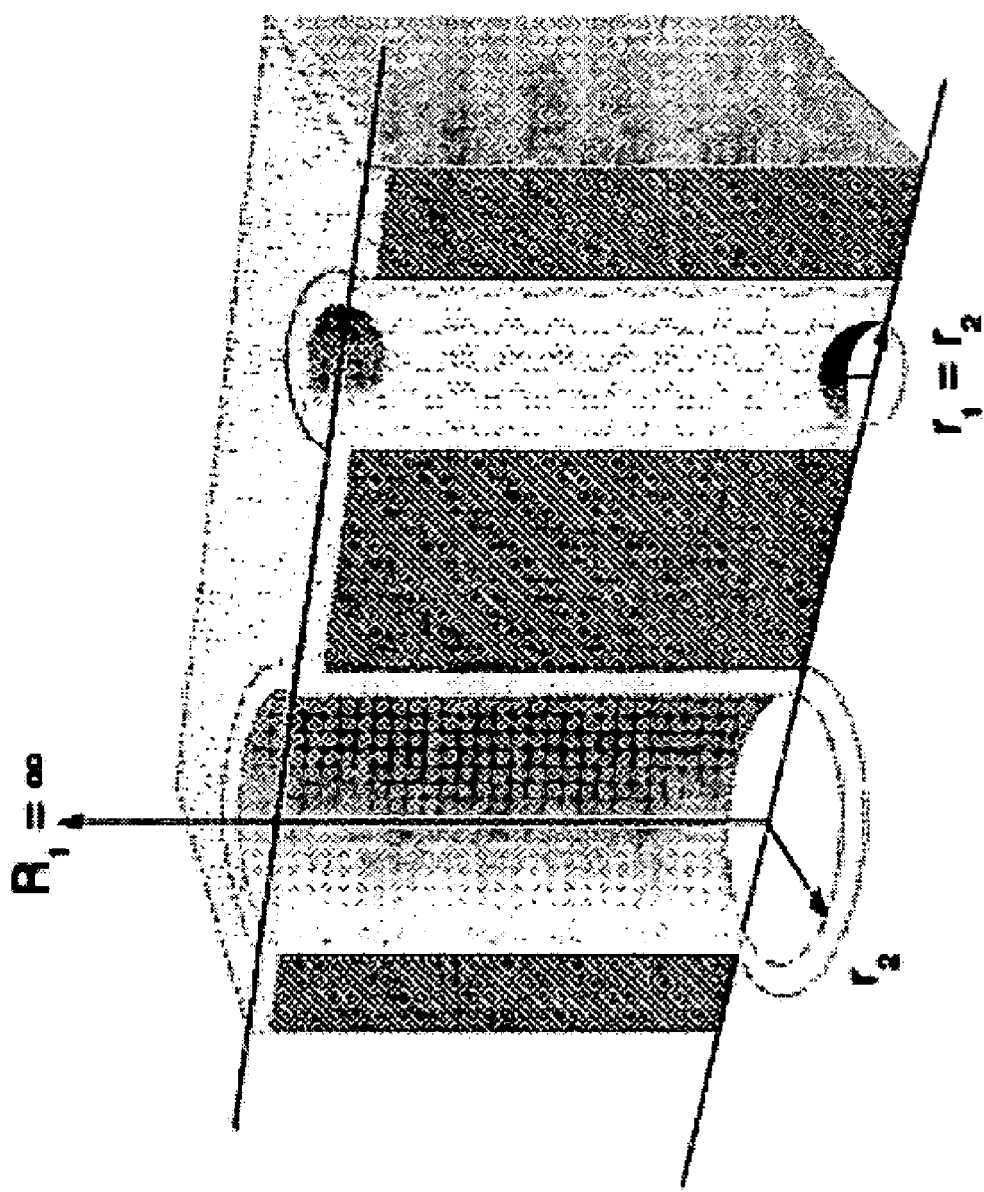
FIG. 5 provides an illustrative diagram that illustrates condensation and evaporation from a pore that is open at both ends.

In Equation (3), $r_m$ in terms of $r_1$ and $r_2$ is expressed by the following Equation (4) and r1 and r2 are defined as illustrated in FIG. 5 (see cited reference number 23):

$$\frac{1}{r_m} = \frac{1}{2}\left(\frac{1}{r_1} + \frac{1}{r_2}\right) \tag{4}$$

For adsorption, $r_2 = \infty$, so Equation (3) is modified to provide the following Equation (5) which is referred to herein as the Kelvin-Cohan adsorption equation:

$$r_1 = \frac{-\gamma v \cos\theta}{RT \ln(P/P_0)} \tag{5}$$

For desorption, $r_1 = r_2$, so Equation (3) is modified to provide the following Equation (6) which is referred to herein as the Kelvin-Cohan desorption equation:

$$r_1 = \frac{-2\gamma v \cos\theta}{RT \ln(P/P_0)} \tag{6}$$

Equations to describe multilayer physisorption on the walls of the pores can be derived from adsorption isotherms on reference materials that have the same surface energy as mesoporous material, but are macroporous in nature. The amount adsorbed is generally converted to a statistically averaged film thickness. The most common models are the Halsey and the Harkins-Jura models. The Halsey model is expressed by the following Equation (7):

$$t = H1 \left[\frac{-H2}{\ln(P/P_0)}\right]^{H3} \tag{7}$$

The Harkins-Jura model is expressed by the following Equation (8):

$$t = \left[\frac{HJ1}{HJ2 - \log(P/P_0)}\right]^{HJ3} \tag{8}$$

For the above equations (7) and (8), the following parameters may be used as defaults in Micrometric ASAP software:

TABLE II

Default parameters for Equations (7) and (8):

| | Value |
|---|---|
| Halsey Parameter | |
| H1 | 3.54 |
| H2 | −5 |
| H3 | 0.333 |
| Harkins-Jura Parameter | |
| HJ1 | 13.99 |
| HJ2 | 0.034 |
| HJ3 | 0.5 |

The Halsey model may be used for modeling the statistical film thickness for embodiments using a $N_2$ adsorbate at 77 K on a silica-based film whereas the Harkins-Jura model may be appropriate for carbon-based films. ASTM standard practice for calculating pore size distributions from $N_2$ isotherms uses the Harkins-Jura model with the parameters provided in Table II. The film thickness of adsorbed $N_2$ also can be estimated from adsorption data on non-porous or macroporous reference materials, since no capillary condensation would be expected until very high relative pressures. For low κ films that are hydrophobic because of the methyl groups incorporated into the film by the use of methyltriethoxysilane, models based on standard isotherms for non-porous hydroxylated silica may be less desirable than one based on a reference isotherm for an appropriately non-porous hydrophobic surface.

There have been a number of procedures suggested for calculating pore size distribution from adsorption/desorption isotherms (e.g., $N_2$ at 77 K) on mesoporous materials. In one embodiment, the procedure employed is the BJH procedure. The model is based on the assumptions that the pore geometry is cylindrical, the pores are non-interacting with each other, and that a meniscus is formed within the pore due to capillary condensation of the adsorbate. The BJH procedure uses an imaginary incremental emptying of the cylindrical pores filled with condensed adsorbate as the pressure is lowered at each data point in the isotherm. The amount of $N_2$ desorbed in the first increment consists of $N_2$ condensate removed from the cores of the pores opened in that increment. The amount of $N_2$ desorbed in each subsequent increment consists of two portions: $N_2$ condensate removed from the cores of the pores opened in that increment, and $N_2$ removed by thinning of the adsorbed layer on the walls of the larger pores already opened in previous increments. The portion of $N_2$ desorbed that results from thinning is calculated first; the $N_2$ remaining (if any) comes from newly opened pores. The volume of the pores opened in each increment is calculated from the amount of $N_2$ condensate removed from the cores of the newly opened pores and the amount of $N_2$ in the adsorbed layer remaining on the walls of the newly opened pores. The procedure of incremental emptying of the pores is used for both the adsorption branch and the desorption branch of the isotherm, even though only the desorption branch was actually created by emptying of the pores.

As described above, the Kelvin equation is used to calculate the radius of the core, and the multilayer statistical film thickness model is used to calculate the thickness of the adsorbed layer. The sum of the two gives the pore radius. The BJH calculation generates a table of pore diameters and incremental pore volumes. The incremental volumes are summed and typically the cumulative volume is plotted as a function of pore diameter to give a cumulative pore volume plot. Because of the nature of the BJH calculation (a incremental emptying starting from the largest pores), the plot normally shows pore volume increasing as the pore diameter decreases.

The concentration of pores is typically viewed in a plot of the absolute value of the slope (dV/dD) vs. the pore diameter. This plot of the derivative of the cumulative pore volume plot is usually called the dV/dD (incremental change in pore volume/incremental change in pore diameter) plot. The dV/dD plot is often used to define the pore diameter; i.e., the pore diameter is the diameter at the maximum in the peak in the dV/dD plot.

Since the incremental pore volume and pore diameter are known for each increment, the incremental pore area can also be determined for the increment assuming cylindrical pores. The incremental areas can be summed and plotted as a function of pore diameter to give a cumulative pore area plot.

The total pore volume and total pore area from the BJH calculations can be combined to give another measure of the pore diameter, the average pore diameter that is calculated from the following Equation (9):

average pore diameter=4×(cumulative pore volume)/(cumulative pore area) (9)

The average pore diameter calculated in this way (4V/A) is similar to the hydraulic radius proposed for a method of pore structure analysis that did not assume any shape for the pores.

The BJH average pore diameter is calculated from the BJH cumulative pore volume and BJH cumulative pore area; the Micromeritics software refers to it as "average pore diameter (4V/A)". The average pore diameter can also be calculated from the Gurvich pore volume and the BET surface area; in that case, the Micromeritics software refers to it as "average pore diameter (4V/A by BET). The Gurvich pore volume is calculated from the total amount adsorbed by capillary condensation by assuming that the adsorbate has the normal molar volume of the bulk adsorbate liquid at the temperature of the experiment.

Another definition of pore size is the median pore diameter; i.e., the pore diameter that corresponds to half the total pore volume in the BJH cumulative pore volume plot. Half of the mesopore volume is in pores larger than the median pore diameter, and half of the mesopore volume is in pores smaller than the median pore diameter. The value for the median pore diameter will depend on the range of pressures over which the isotherm was collected and the range of pore diameters, which were used for the BJH calculations. In summary, historical definitions of pore diameter based on the pore size distribution calculated from adsorption/desorption isotherms using the BJH procedure include: Pore diameter at the peak in the dV/dD plot; Average pore diameter (4V/A, "hydraulic radius"); and Median pore diameter (pore diameter at half the mesopore volume). The choice of which definition to use depends on the application for the porous material.

Many other classical procedures are available, such as for example, using a series of samples with different pore diameters to compare the relative pressures for capillary condensation and evaporation of $N_2$ at 77 K to the pore diameter using MCM-41 mesoporous molecular sieves. Examples of procedures that can be used include those described in the following references: Dubinin, M. M.; Radushkevich, L. V. *Proc. Acad. Sci. USSR* 1947, 55, 331; Cranston, R. W.; Inkley, F. A. "The Determination of Pore Structures from Nitrogen Adsorption Isotherms"; *Advances in Catalysis;* Academic Press: New York, 1957; Vol. 9, pp 143-154; and Kruk, M.; Jaroniec, M.; Sayari, A. "Application of Large Pore MCM-41 Molecular Sieves To Improve Pore size Analysis Using Nitrogen Adsorption Measurements"; *Langmuir* 1997, 13, 6267-6273. In certain embodiments classical models may not be accurate at mesopore diameters below 70 Å, given that the assumption for the wall density of the particular samples is correct. In these embodiments, the classical equations are used as a purely empirical way to fit the data. In that way, there would be no need to attempt to justify why the Kelvin-Cohan desorption equation should be used on the adsorption branch of the isotherm. Even then, an additional 3 Å needed to be added to the pore radius to match the pore diameters derived from the diffraction results. This empirical equation is appropriate for characterizing the pore diameter using the adsorption branch of the isotherm for samples exhibiting hysteresis, and using either the adsorption branch or the desorption branch of the isotherm for samples that do not exhibit hysteresis. The procedure is simple and straightforward, requiring only a small modification to use the classical BJH calculations to obtain pore size distributions. The approach has been referred to as the Kruk-Jaroniec-Sayari (KJS) approach.

The BJH procedure discussed above employs classical macroscopic thermodynamic concepts for characterizing adsorption and condensation in mesoporous materials. A more rigorous, perhaps more intellectually appealing solution to the theoretician, is provided in the use of procedures based on microscopic theoretical models to calculate the isotherm from molecular interactions, such as Density Functional Theory (DFT), methods of molecular simulation, such as, for example, Monte Carlo and Molecular Dynamics. Although the microscopic theories are known in the prior art, they are employed in a novel manner in one aspect of the procedure described herein. The Density Functional Theory (DFT), for instance employs microscopic concepts for describing inhomogeneous fluids. DFT calculates the density profiles of a fluid interacting with a porous surface of a given geometry (slit pores, cylindrical pores, etc.) in equilibrium with the bulk fluid phase at a given pressure and temperature using inter-molecular fluid-fluid and fluid-solid interactions. The so-called Non-Local Density Functional Theory (NLDFT) accounts for the fluid-fluid interactions in a way that produces the strong "oscillations" of fluid density at the solid-fluid interface, representing the layering close to the pore walls that reflects multilayer adsorption, which is needed for an accurate description of adsorption particularly in narrow micropores.

The parameters in the expression for the fluid-fluid interactions are obtained by matching the bulk properties; the parameters in the expression characterizing the energetics of the fluid-solid interactions are obtained by matching the points in an adsorption isotherm on a representative non-porous solid. The density profiles for all locations in the pore for a given temperature and pressure are obtained by minimizing the free energy of the system (or more specifically, the grand Helmholtz free energy, or grand potential functional), and the amount adsorbed is obtained by summing over the density profiles. The adsorption isotherm for a given pore geometry is constructed by performing this calculation at discrete intervals over the whole range of relative pressures from zero to one. The validity of the DFT calculations has been established by comparing such calculated isotherms to measured isotherms on materials with narrow pore size distributions, such as MCM-41 mesoporous molecular sieves, whose pore size has been determined by other methods.

In certain embodiments, capillary condensation and desorption can be measured using the DFT model in siliceous mesoporous molecular sieves with cylindrical channels and characterized their pore structure using NLDFT. In these embodiments, calculations were performed using Lennard-Jones type potentials for the fluid-fluid and fluid-solid interactions. For the fluid-fluid interactions, the fitted parameters included the well depth and the distance parameter of the Lennard-Jones potential, as well as the diameter of hard spheres for repulsion; the cutoff distance at which the Lennard-Jones potential was truncated was kept constant. For the fluid-solid interactions, the fitted parameters included an energetic parameter and a distance parameter. The parameters for the fluid-fluid interactions were chosen to reproduce bulk properties at low temperatures such as liquid-gas coexistence densities, saturation pressure, and surface tension of free liquid-gas interface, the last property of particular relevance for capillary condensation in pores, as discussed above under the classical models. The parameters for the fluid-solid interactions were obtained by fitting calculated adsorption isotherms on an open surface to standard experimental isotherms on non-porous oxides.

The energy minimization to obtain the adsorbate density distribution depends on the starting parameters. If the energy minimization is performed starting with unfilled pores, and the results for each relative pressure are used as the starting points for the next higher discrete relative pressure, the results differ from the case where energy minimization is performed starting with filled pores and proceeding to lower relative pressures. The two cases can be seen in the plot of grand potential vs. $P/P_0$ in FIG. 6 (see cited reference number 36) (bottom) for the adsorption of Ar at 87.3 K on an MCM-41 type material. The experimental isotherm, which contains a wide hysteresis loop, is compared to the isotherms calculated by NLDFT in FIG. 6 (id.) (top).

For the case of adsorption for this example, solutions correspond to the adsorption and desorption branches of the isotherm respectively. The solution with a lower value of the grand potential corresponds to the stable branch of the isotherm and the solution with a larger value of the grand potential corresponds to the metastable branch of the isotherm. The minimum for the grand potential follows a smooth curve as a function of increasing $P/P_0$. It crosses the minimum grand potential for the desorption branch at a $P/P_0$ of about 0.5 and becomes metastable. The metastable portion terminates at a discontinuity at a $P/P_0$ of about 0.58 that is termed a vapor-like spinodal where the limit of stability of the metastable state is reached and the fluid spontaneously condenses into a liquid-like state. The vapor-like spinodal corresponds to the condensation step in the adsorption isotherm. The minimum for the grand potential then finishes along the stable desorption branch.

For the case of desorption, the minimum for the grand potential follows a smooth curve as a function of decreasing $P/P_0$. It crosses the minimum grand potential for the adsorption branch at the $P/P_0$ of 0.5 and becomes metastable. The metastable portion terminates at a discontinuity at a $P/P_0$ of about 0.2 that is termed a liquid-like spinodal where the limit of stability of the metastable state is reached and the fluid spontaneously evaporates into a vapor-like state. The minimum for the grand potential then finishes along the stable adsorption branch.

For open-ended cylindrical pores, the metastable liquid-like states along the desorption branch are apparently never observed, and evaporation/desorption occurs when the desorption branch of the grand potential meets the adsorption branch at the equilibrium point. For the case of equilibrium desorption, the minimum for the grand potential follows a smooth curve as a function of decreasing $P/P_0$. At the equilibrium point, it crosses from the stable desorption branch to the stable adsorption branch. The minimum for the grand potential then finishes along the stable adsorption branch.

FIG. 6 illustrates the correspondence between the argon relative pressure calculated for spinodal condensation and the condensation step in the adsorption branch of the isotherm, and the correspondence between the relative pressure calculated for the equilibrium transition and the evaporation/desorption step in the desorption branch of the isotherm. FIG. 6 also illustrates the agreement between the pore diameter of 48 Å used for the NLDFT calculations and the nominal pore diameter of 51 Å determined for the MCM-41 sample using an equation based on geometrical consideration of the ordered honeycomb structure characteristic of MCM-41 that incorporated interplanar spacing from X-ray diffraction data, pore volume from nitrogen adsorption data, and pore wall density assumed to be 2.2 $cm^3/g$, the value for amorphous silica.

In certain embodiments, nitrogen can be used as the adsorbate. The NLDFT results for nitrogen agree with the pore diameter determined by other means.

Typical mesoporous materials possess a distribution of mesopore sizes. To match the experimental isotherm, it is assumed that the total isotherm consists of the sum over the range of pore sizes of the individual "single pore" isotherms, each multiplied by its relative amount, termed the Generalized Adsorption Isotherm (GAI) equation given by the following Equation (10):

$$N(P/P_0) = \int_{W_{MIN}}^{W_{MAX}} N(P/P_0, W) f(W) dW, \quad (10)$$

where $N(P/P_0)$ experimental adsorption isotherm data; W=pore width; $N(P/P_0,W)$=isotherm on a single pore of width W; and f(W)=pore size distribution function.

The set of "single pore" isotherms at discrete pore diameters for a given system consisting of adsorbate, adsorbent, pore geometry, and temperature can be referred to as a kernel. The pore size distribution can be obtained by solving the GAI equation numerically using a non-negative least squares algorithm. Although the method described herein uses DFT, in this case the DFT calculation itself would not be done to calculate the pore size distribution for each sample from its experimental isotherm. Instead, a kernel of single pore isotherms might be initially calculated using DFT, and only the GAI equation might be solved for each experimental isotherm using this previously calculated kernel.

The relative pressures for the equilibrium desorption and spinodal condensation transitions predicted by NLDFT for cylindrical pores from 20 to 1000 Å were compared to those predicted by the Kelvin-Cohan model for adsorption with a "cylindrical meniscus" and desorption with a hemispherical meniscus. In the limit of very large pores, the NLDFT line for equilibrium transition asymptotically approaches the Kelvin-Cohan line for desorption, and the NLDFT line for spinodal condensation asymptotically approaches the Kelvin-Cohan for adsorption. As the pore size decreases, even for pores as large as 100-200 Å, the differences between the NLDFT calculations and the Kelvin-Cohan calculations become appreciable, suggesting that the classical macroscopic model cannot adequately account for the surface forces.

The DFT theory may account for the compression of $N_2$ condensed by capillary action in the pores. This phenomenon leads to additional $N_2$ uptake at high $P/P_0$ that can be seen in the calculated isotherms in FIG. 6. The calculated isotherms do not level off above the point of capillary condensation in these idealized pores, but the amount adsorbed continues to gradually increase as the relative pressure increases. The density of bulk liquids can be increased very little by compression. However, the density of liquid condensed in capillaries can be increased by compression because the capillary condensed liquid is under tension. Thus, it is believed that increasing the pressure will compress the $N_2$ in the pores and increase the density. Increasing the density for the same pore volume requires additional uptake of $N_2$. The software to calculate pore size distribution from adsorption isotherms based on DFT calculations is commercially available, such as, for example, Quantachrome Autosorb or Micromeritics DFT Plus software. Although DFT kernels are primarily available for $N_2$ at 77 K and Ar at 87 K, they can be developed for other adsorbates at other temperatures.

In step 140, a maximum pore diameter may be determined from the incremental pore volume as a function of pore diameter. The BJH procedure is used as an example of the procedure for calculating the pore size distribution, but other models and procedures may be applicable as well. The BJH procedure uses the $N_2$ adsorption/desorption isotherm at 77 K to calculate incremental pore volume as a function of pore diameter, from which a plot of cumulative pore volume as a function of pore diameter can be obtained. A number of different definitions of pore diameter can be extracted from this calculation such as the peak in the dV/dD plot, the average pore diameter, or the median pore diameter. For most applications in the past, one desired a definition of pore diameter that accounted for the pore size that characterized the majority of the pore volume. The peak in the dV/dD plot is often a good indication of this pore diameter, particularly if there is a sharp step in the cumulative pore distribution plot. For applications in which fluid flow through the pores is of primary interest, the average pore diameter (4V/A), similar to the concept of hydraulic radius, may be most useful, particularly if there is a broad distribution of pore sizes. The median pore diameter, the pore diameter at half the mesopore volume, has also been used.

Traditional definitions of pore diameter such as the average pore diameter may be appropriate for applications involving fluid flow, but do not appear entirely satisfactory for determining whether killer pores are present in low κ materials for applications as interlevel dielectrics. Definitions based on an average or median pore diameter might suffice if the pore size distribution around the average remains constant from one film formulation to another; then the magnitude of the average diameter will be correlated with the size of the largest pores. A new definition is proposed, a maximum pore diameter, which can be used to detect the presence of "killer" pores by comparison to the critical defect size established for a given low κ technology node. One way of determining a maximum pore diameter might be based on a cutoff in the slope of the plot of cumulative pore volume vs. pore diameter.

Nitrogen isotherms at 77 K on typical 1.9 κ films prepared from standard formulations for silica-based films using surfactant as porogen exhibit a Type IV isotherm with a type H2 hysteresis loop, which has a broad adsorption branch, an almost flat plateau, and a steep desorption branch. Many inorganic oxide gels show this type of hysteresis loop. The pore structures in these materials are complex and reported to be made up of interconnected networks of pores of different size and shape. The steep desorption branch of the type H2 hysteresis loop has been attributed to network percolation effects. Since the isotherm shape indicates interconnected ink-bottle pores, it seems appropriate to use the adsorption branch of the isotherm for the calculations, because the historical use of the desorption branch would only characterize the pore necks.

In certain embodiments, a maximum pore diameter may be used for determining whether killer pores are present in low κ films for applications as interlevel dielectrics in integrated circuit devices. If the desorption branch of the isotherm would be used to define the pore diameter, as historically practiced, the pore size distribution would be narrow because of the sharp step in the isotherm. In that case, little benefit would be gained by defining a maximum pore diameter because the value would be close to any one of the values historically used for defining the size of the majority of the pores, whether it would be the peak in the dV/dD plot, the average pore diameter, or the median pore diameter. However, since it has been determined that the adsorption branch is appropriate for characterizing the pores of low κ films, the pore size distribution will be broad, and there will be a need for defining a maximum pore diameter. The absence of killer pores might then be determined by comparing the maximum pore diameter to the critical defect size that has been established for a given low κ technology node.

To the extent that a definition of pore diameter that attempts to represent the majority of the pore volume is also an indication of killer pores, it might presumably be correlated with the ability to integrate a film in a device. The distribution of pores might be represented by a standard type distribution around the pore diameter. For instance, a Gaussian distribution of variable width and height for the plot of incremental uptake vs. pore diameter using the Kelvin equation for toluene adsorption measured by X-ray reflectivity (XRP) may be used in one embodiment. In another embodiment, a gamma distribution function of spherical voids characterized by two parameters for modeling diffuse X-ray reflectivity data. In either embodiment, the magnitude of the average diameter would be correlated with the size of the largest pores. The models of pore size distribution could also be used to determine a maximum pore diameter by using a cutoff at a specified pore volume (e.g., 99% of the total pore volume). However, the assumptions of a shape for the distribution and that the shape remains constant from one film formulation to another may not be valid.

In other embodiments, a maximum pore diameter may be determined directly from the pore size distribution calculated using the BJH procedure without assuming a shape for the distribution. In one embodiment, the maximum pore diameter may be defined in terms of a cutoff in the pore size distribution such that there is an "insignificant" volume of the total porosity in pores with diameter larger than the maximum.

Likewise, the sensitivity of a method and procedure for determining the minimum volume in killer pores might be referred to as a killer pore volume absence detection limit. Normally, detection limits address the ability of a technique to detect the presence of a characteristic. In this case, the object is to establish the absence of killer pores when other phenomena might suggest their presence. Put another way, interferences from these phenomena might incorrectly indicate the presence of killer pores.

There are many ways in which a maximum pore diameter might be defined. Some exemplary ways that the maximum pore diameter may be defined are as follows: (1) a pore volume cutoff that uses an absolute value of the pore volume that corresponds to an "insignificant" volume in pores larger than the cutoff referred to herein as "absolute pore volume cutoff", (2) a pore volume cutoff that corresponds to a percent of the total volume that corresponds to an insignificant volume in pores larger than the cutoff (for example, a pore volume cutoff of 5% of the total volume) referred to herein as "percent pore volume cutoff", and (3) the slope of the cumulative pore distribution plot that corresponds to the point at which the adsorption branch of the isotherm meets the desorption branch referred to herein as "cutoff pore distribution slope". These options will be evaluated in this section using low κ films from three different formulations.

There are at least three ways uptake is observed in the isotherms at high $P/P_0$: (1) as a sharp upturn for last data point, (2) as a sharp upturn above $P/P_0$ of about 0.85, typically observed only for powders obtained by scraping the film off wafer, and (3) as a gradual slope above a $P/P_0$ of about 0.7, the point at which the adsorption branch meets the desorption branch. Each of these will be considered in turn.

A sharp upturn is often observed for the last data point in the $N_2$ isotherm for low κ films. Since the last point is collected at a relative pressure close to 1, it often shows the effects of liquid condensation because of uncertainty in the pressure and temperature measurements, as well as variability in the bath temperature and atmospheric pressure that will change the value of the saturation pressure, $P_0$. The last point in the isotherm can be mathematically eliminated by judicious choice of the upper pore diameter limit for the pore diameter range used for the BJH calculation. Alternatively, the last isotherm data point in the ASAP pressure table could just be deselected for the BJH calculation.

The sharp upturn above $P/P_0$ of about 0.85, typically observed only for powders obtained by scraping the low K film off the wafer, has been attributed to capillary condensation in the interstices between powder particles. In fact, this is one of the unexpected benefits of on wafer analysis. On wafer measurement allows quantification of the maximum pore diameter without complications arising from condensation of the adsorbate in the interstices between particles that results in a sharp upturn in the isotherm at high $P/P_0$ that cannot be distinguished from the presence of large pores in the pore size distribution calculations.

One explanation for the gradual slope above a $P/P_0$ of 0.7 may be the result of compression of $N_2$ already condensed in the pores. The density of bulk liquids can be increased very little by compression. However, the density of liquid condensed in capillaries can be increased by compression because the capillary condensed liquid is under tension. Thus, increasing the pressure will compress the $N_2$ in the pores and increase the density. Increasing the density for the same pore volume requires additional uptake of $N_2$. The phenomenon is observed as a gradual positive slope in the isotherm plot of increasing volume of $N_2$ adsorbed as a function of increasing $N_2$ pressure.

An absolute pore volume cutoff could be used to define the maximum pore diameter in the following way: the pore volume in pores with diameters greater than the maximum pore diameter is less than a certain value cc/g (e.g., 0.01 cc/g). The pore volume cutoff might give an indication of the amount of the film that might fail during integration as low κ interlevel dielectrics in integrated circuit devices.

A percent pore volume cutoff could be used to define the maximum pore diameter in the following way: the pore volume in pores with diameters greater than the maximum pore diameter is less than a certain % of the total pore volume. A percent of the total pore volume would be a criterion that might be more readily understood in terms of what fraction of the film would be susceptible to failing integration, however the absolute value of the volume would differ depending on the dielectric constant of the film. Since the dielectric constant of materials competing for a given node might be expected to fall within a narrow range, the total pore volume would fall within a range, and the use of a percent of the total pore volume might be readily accepted.

One way of eliminating the effects of the variability of the magnitude of the gradual slope in the isotherm at high $P/P_0$ is to use the slope of the cumulative pore volume plot or the cutoff pore distribution slope. The slope of the plot of cumulative pore volume vs. pore diameter could be used in the following way: the maximum pore diameter is the pore diameter at which there is a sharp increase in the magnitude of the (negative) slope (e.g., at a slope of 0.001 or 0.002 cc/g-Å) as the pore diameter decreases; the pore volume in pores larger than this would be variable from sample to sample, and could be reported as an absolute pore volume, or as a percent of the total pore volume. The slope is more readily observed as a dV/dD cutoff in the dV/dD plot. Note that the slope is negative in the cumulative pore volume plot since the incremental volumes are summed for the BJH calculations starting at high $P/P_0$, but that the value is positive in the dV/dD plot.

One procedure to determine a maximum pore diameter from the incremental pore volume as a function of pore diameter could be to calculate the cumulative pore volume as a function of pore diameter from the incremental pore volume as a function of pore diameter and determine a maximum pore diameter as the pore diameter above which there is no porosity. In one embodiment of this procedure, the DFT model is used because of its ability to account for compression of $N_2$ condensed in the pores.

If the classical models are used, then a pore volume cutoff, either absolute, or as a percent of the total pore volume, might be used. However, maximum pore diameters calculated in this way are not very reproducible if the pore volume cutoff is chosen to give a pore diameter expected for the closure of the adsorption branch with the desorption branch. In that case, the procedure could be to calculate the cumulative pore volume as a function of pore diameter from the incremental pore volume as a function of pore diameter and determine a maximum pore diameter using a cutoff based on the slope of the plot of cumulative pore volume as a function of pore diameter that is easily visualized in the dV/dD plot. The preferred slope appears to be about 0.002 cc/g-Å as a value that gives a pore diameter expected for the closure of the adsorption branch with the desorption branch, a small volume in pores larger than the maximum pore diameter, and that is reasonably reproducible.

In step 150, the presence of killer pores may be determined by comparing the maximum pore diameter to the pore diameter that has been established for killer pores in a given application. The methodology for determining the presence of killer pores comprises identifying a maximum pore diameter for the sample. If the size of killer pores is known for a given application, then a maximum pore diameter greater than the killer pore diameter indicates the presence of killer pores. Alternatively, a maximum pore diameter less than the killer pore diameter indicates the absence of killer pores. If the size of killer pores is not known for a given application, a series of samples could be prepared with different maximum pore diameters, the samples could be submitted for application testing, for example for integration as interlevel dielectrics, and the maximum pore diameter correlated with the ability to survive integration. The killer pore size for that application would be greater than or equal to the maximum pore diameters of the samples that failed to survive integration, assuming all other parameters can be kept constant.

Although the objective could be to merely correlate maximum pore diameter with the ability to survive integration, the definition would be more readily acceptable if the actual value of the pore diameter is reasonable compared to what the industry expects; i.e., significantly less than the line width. The line width, of course, will depend on the technology node at which the low κ porous film is being introduced. The International Technology Roadmap for Semiconductors (ITRS) technology node line width (nm) is defined as the DRAM ½ pitch (nm), where the pitch is the sum of the space in between and the width of the metal lines connecting DRAM bit cells. Some have assumed that the killer pore size is equal to the critical defect size. In certain embodiments, the critical defect size is generally ½ the line width. A definition of maximum pore diameter that will give reasonable pore diameters will depend on the procedure and model used to calculate the pore size distribution and the volume chosen for defining the cutoff.

In comparison to other techniques suggested for characterizing the porosity of open pore low κ films, the present method, encompassing both the experimental step of packing thins strips of wafers coated with films in the adsorption cell and the analysis step of determining a maximum pore diameter by a dV/dD cutoff, offers several advantages, particularly for establishing the absence of "killer" pores. The method measures the whole wafer as compared to other techniques such as EP and XRP that analyze only a spot even if the entire film was exposed to an adsorbate. The method is not constrained by the type and number of observations, particularly compared to SANS and XRR, to be required to assume a shape for the distribution of pores around the average pore diameter, but can calculate multiple points to characterize the pore size distribution directly from the adsorption data. Since the film remains intact on the wafer, there is no large upturn in the isotherm at $P/P_0$ above about 0.85, attributed to condensation of $N_2$ in the interstices between powder particles, yet that is nevertheless indistinguishable from killer pores, and thus would prevent the absence of killer pores from being conclusively established. The use of DFT when the goal is identifying killer pores offers a significant advantage because it accounts for the compression of adsorbate condensed in the pores by capillary action that results in a gradual slope at high $P/P_0$.

FIG. 2 provides a process flow diagram of another embodiment of the method of the present invention. FIG. 2 has similar process steps as FIG. 1 except steps 110 and 130 differ as reflected in steps 110' and 130'. Referring to FIG. 2, in step 110' an adsorption isotherm is measured on the porous film on substrate in adsorption cell by exposing the porous film on the substrate to adsorbate vapor. In this embodiment of the invention, measurement of the adsorption/desorption for the film on the substrate is not limited to the volumetric technique as required in FIG. 1. The isotherm can be measured by other techniques known in the literature, such as EP, XRP, etc., or yet to be discovered. The operating conditions for the steps in these processes can be found in the references cited herein. In step 130', the incremental pore volume is calculated as a function of pore diameter from the measured adsorption isotherm or isobar using a (mathematical) procedure that incorporates a model that relates pressure for capillary condensation to pore size and that accounts for compression of the adsorbate capillary condensed in the pores at pressures above the condensation pressure. The use of DFT has been described above under step 130 of the first embodiment of the invention. DFT is an example of a model that relates pressure for capillary condensation to pore size and that accounts for compression of the adsorbate capillary condensed in the pores at pressures above the condensation pressure. The use of DFT is preferred when the goal is identifying killer pores for low κ applications because it accounts for the compression of adsorbate condensed in the pores by capillary action that results in a gradual slope at high $P/P_0$ and does not have to (falsely) attribute the gradual slope to additional porosity in large pores.

FIG. 3 provides a process flow diagram of yet another embodiment of the method of the present invention. Referring to FIG. 3, in step 110'', an adsorption isotherm is measured using any method on a porous film on substrate in adsorption cell by exposing the porous film on the substrate to adsorbate vapor. In this embodiment of the invention, measurement of the adsorption/desorption for the film on the substrate is not limited to the volumetric technique described herein. The isotherm can be measured by other known techniques, such as but not limited to EP and XRP. The operating conditions for the steps in these processes can be found in the references cited above. In order to be used as a quality control test or process control method, significant modifications may have to be made to the apparatus and methods for measuring adsorption of adsorbates by the film on the substrate, such as might be required for incorporating the intact wafer, using an adsorbate and isotherm temperature other than $N_2$ at 77 K (although the conditions must still be such that result in capillary condensation in the pores), measuring fewer adsorption points than might be measured for a full pore size distribution, etc. As discussed above under step 90, a void volume determination might not be required each time a sample is measured. It might be determined once and then the same-value manually entered for each sample.

In step 150", the presence or absence of killer pores may be determined by using a method that was developed using a model that relates pressure for capillary condensation to pore size and that accounts for compression of the adsorbate capillary condensed in the pores at pressures above the condensation pressure. If the method described herein is used as part of a quality control test, multiple films will be prepared using the same film forming solution and the same process. It may not be desirable to measure a full isotherm and calculate a full pore size distribution for each film measured. It may not be necessary to solve the GAI equation using a DFT kernel for each isotherm for each film measured to determine whether killer pores are present. For quality control purposes, a cutoff slope in the isotherm referred to herein as cutoff adsorption isotherm slope might be determined by using DFT on a reference material to account for compression of $N_2$ condensed in the pores. The comparison of the adsorption isotherm to the cutoff adsorption isotherm slope may be used to determine the presence of one killer pore. In certain instances, the method may measure a few data points at high $P/P_0$ on the adsorption isotherm of the sample and to the cutoff adsorption isotherm slope of the reference material.

In step 160, the film may be accepted or rejected the film based on the presence of killer pores. This method can be used as part of a quality control test. Based on the presence of killer pores, the film can be accepted or rejected. Depending upon the presence of killer pores in step 150", in step 170 the process parameters may be changed. The method can be used as part of a process control method for controlling the fabrication process of the film on the substrate. Based on the presence of killer pores, the process control parameters can be modified. Fabrication process parameters for spin-on films include spin speed, heating temperature, time for heating, etc. Fabrication process parameters for CVD films included, for example, heating temperature, time for heating, and other parameters.

EXAMPLES

Example 1

Spin-on Low κ Film Using Surfactant as Porogen and BJH/Kelvin as Procedure/model for Capillary Condensation The following example shows that it is possible to measure adsorption/desorption isotherms volumetrically on a film on a substrate. It also shows a new definition of pore diameter that can be used for determining whether killer pores are present. The film forming mixture was prepared in a high-density polyethylene bottle by adding 50/50 by weight methyltriethoxysilane/tetraethoxysilane solution, propylene glycol propyl ether, and surfactant. The mixture was shaken briefly. An aqueous solution of 96 wt % 0.1 M nitric acid and 4 wt % 2.4 wt % aqueous tetramethylammonium hydroxide, was added. The bottle was capped and shaken for 30 to 60 seconds. The solution was aged in the capped bottle at ambient temperature for at least 2 hours.

A film of the mixture was deposited by spin-coating a 1.2 milliliter (mL) sample on a 4-inch wafer with 0.005-0.020 ohm-cm resistivity using a Laurell WS-400A-8TF/Lite spin processor with a spinning program of 7 seconds at 500 revolutions per minute (rpm) (dispense speed), then 40 seconds at 1800 rpm. The film was cured before the end of the day by placing the spin-coated wafer on hot plates at 90° C. for 1.5 minutes (min), 180° C. for 1.5 min, and 400° C. for 3 min. The silicon (Si) wafer was weighed using a 4-place balance (Mettler PM 2000) before spin-coating and after curing to determine the weight of the spin-coated low κ film. Typically 5 films were spun for each example with a target thickness of 1.5 μm.

Table III summarizes the target dielectric constant, the formulation of the film-forming solution, and the preparation conditions for the low κ films used in this study.

The dielectric constant and thickness indicated in the sample description are target values. The surfactants used as porogens were Triton X-114 and Pluronic L-101. The solvent was propylene glycol propyl ether (PGPE) unless otherwise indicated in the sample description. The aging time is the time between preparing the formulation and spinning. R.H. is the relative humidity of the room.

TABLE III

| | | Formulations and Preparation for low k Films | | | | | | | |
|---|---|---|---|---|---|---|---|---|---|
| Sample | Sample description | TEOS/ MTES, g | solvent, g | surfactant, g | $HNO_3$/ TMAH, g | aging, h | filter | spin temp, °F. | spin R.H., % |
| Sample 1 | 1.9k, X-114, 1 μm | 2.25 | 2.0 | 0.879 | 1.25 | 16 | No | 73 | 23 |
| Sample 2 | 1.9k, L-101, 1.4 μm | 2.25 | 2.0 | 0.55 | 1.25 | 2 | No | 73 | 22 |
| Sample 3 | 2.2k, X-114, 1.5 μm | 2.7 | 2.4 | 1.055 | 1.5 | 2 | No | 73 | 2 |
| Sample 4 | 2.7k, X-114, 1.5 μm | 2.25 | 2.0 | 0.225 | 1.25 | 2 | No | 74 | 15 |
| Sample 5 | 1.9k, X-114, 1 μm | 2.25 | 2.0 | 0.879 | 1.25 | 2 | No | 73 | 22 |
| Sample 6 | 1.9k, X-114, 1.5 μm | 18.00 | 16.0 | 7.03 | 10.00 | 72 | No | 73 | 22 |

Volumetrically measured adsorption isotherm using $N_2$ at 77 K

Three 4-in Si wafers spin-coated with the same formulation were scored with a diamond scribe and broken into strips 0.5 to 1.2 cm wide using a specially designed Plexiglas jig. Table IV shows the size distribution for each wafer so they stack inside the tube as easily as possible to maximize the sample weight in the fixed volume.

TABLE IV

Distribution of strips

| Number of strips | size of strips, mm |
|---|---|
| 3 | 5 |
| 1 | 6 |
| 4 | 10 |
| 2 | 13 |
| 1 | 12 |

The strips (including any small fragments because they were included in the sample weight), containing a total of about 20-30 mg low κ film, were loaded into a slightly larger diameter (¾-in o.d.) than normal quartz adsorption cell that was 23 cm long. A borosilicate glass filler tube (13.9 mm×130 mm) was added to reduce the remaining void volume of the cell. The sample tube was attached with an ultratorr fitting to a reducing union for connection to a Micromeritics Accelerated Surface Area and Porosimetry (ASAP) system 2010. A SealFrit™ fitting was inserted into the smaller end of the reducing union to allow the sample tube to be removed after backfilling with He without exposure to atmosphere.

The sample was pretreated at 150° C. in dynamic vacuum ($<10^{-4}$ torr) on the analysis port of the ASAP 2010. The Isothermal Jacket™ that acts as a wicking sleeve supplied with the instrument to act as an isothermal jacket was bored out so the larger tubes could fit inside. The Isothermal Jacket was placed around the adsorption cell. A high quality dewar was used to contain the liquid nitrogen bath for the sample cell because of the long times required for isotherms with a large number of data points. A standard volumetric adsorption/desorption isotherm for $N_2$ at 77 K was measured on the ASAP 2010, which measures the isotherm in general accordance with ASTM method D-4222. Table V summarizes the samples used for the isotherms.

TABLE V

Adsorption/Desorption Isotherms

| sample number | sample description | comments |
|---|---|---|
| Sample 2 (3 films) | 1.9k, L-101, 1.4 μm | 20 mg weight, repeat with 172 pts |
| Sample 6 (3 films) | 1.9k, X-114, 1.5 um | 24.2 mg weight, repeat with 160 pts |

FIG. 7 displays the adsorption/desorption isotherm for $N_2$ at 77 K for samples prepared using Triton X-114 and Pluronic L-101 surfactants as porogens. The low κ film exhibits a Type IV isotherm with a type H2 hysteresis loop, which has a broad adsorption branch, an almost flat plateau, and a steep desorption branch. Many inorganic oxide gels show this type of hysteresis loop. The pore structures in these materials are complex and reported to be made up of interconnected networks of pores of different size and shape. The steep desorption branch has been attributed to network percolation effects. A pore diameter calculated using a model for capillary condensation from the desorption branch of the isotherm would appear to be inappropriate for characterizing this type of open pore low κ films since it would only give the size of the percolation pores. Consequently, the adsorption branch of the isotherm was used for calculating the pore size distribution.

One of the benefits of on-wafer analysis is that the isotherm does not exhibit a sharp upturn at $P/P_0$ greater than about 0.85 attributed to condensation of adsorbate in the interstices between powder particles. However, the isotherm still exhibits additional uptake above a $P/P_0$ of about 0.7. The uptake for the last data point can confidently be attributed to condensation of bulk phase liquid $N_2$ because of very small differences in control and measurement of temperature and pressure. However, there is also a gradual slope in the isotherm above a $P/P_0$ of about 0.7. As discussed previously, adsorption in this region may not be caused by capillary condensation in large pores. However, a procedure and model that is unable to account for the slope in another manner will be limited in its sensitivity for determining the minimum volume in killer pores. This might be termed a killer pore volume absence detection limit.

Calculate the Incremental Pore Volume as a Function of Pore Diameter from the Volumetrically Measured Adsorption Isotherm Using BJH as the Procedure and Incorporating the Kelvin-Cohan Equation as the Model that Relates Pressure for Capillary Condensation to Pore Size The BJH procedure was performed with Micromeritics Instrument Corporation ASAP 2010 Version 5.02 software to calculate the incremental volume as a function of pore diameter from the volumetrically measured adsorption branch of the isotherm. The Kelvin-Cohan desorption equation (Option F=0 in the ASAP software) was used as the model to relate pressure for capillary condensation to pore size. The standard ASAP parameters for the Halsey equation were used to model the statistical film thickness. All the data points were selected in the ASAP pressure table for the BJH calculation. The range of pore diameters selected for the calculation was 10-3000 Å. The incremental volume as a function of pore diameter was summed to give a cumulative volume as a function of pore diameter. FIG. 8 shows a plot of the cumulative pore volume as a function of pore diameter for the adsorption branch of the isotherm.

The plot of cumulative pore volume as a function of pore diameter shows most of the pore volume is in pores smaller than about 60 Å in diameter. The BJH model is unable to account for the slope in the isotherm at $P/P_0$ about 0.7 by any other manner than attributing it to porosity at large pore diameters. Thus the sensitivity for determining the minimum volume in killer pores, or killer pore volume absence detection limit, will be greater than about 0.02 cc/g, or several percent of the total mesopore volume, although still significantly better than if the measurement had been determined using the powder resulting from scraping the film off the wafer.

Determine a Maximum Pore Diameter from the Incremental Pore Volume as a Function of Pore Diameter Using dV/dD Cutoff One way of determining a maximum pore diameter that will eliminate the effects of the variability of the magnitude of the gradual slope in the isotherm at high $P/P_0$ is to use the slope of the cumulative pore volume plot, although this will not change the killer pore volume absence detection limit. The slope of the plot of cumulative pore volume vs. pore diameter could be used in the following way: the maximum pore diameter is the pore diameter at which there is a sharp increase in the magnitude of the (negative) slope (e.g., at a slope of 0.001 or 0.002 cc/g-Å) as the pore diameter decreases; the pore volume in pores larger than this would be variable from sample to sample, and could be reported as an absolute pore volume, or as a percent of the total pore volume. The slope is more readily observed as a dV/dD cutoff in the plot of dV/dD vs. pore diameter. Note that the slope is negative in the cumulative pore volume plot since the incremental volumes are summed for the BJH calculations starting at high $P/P_0$, but that the value is positive in the dV/dD plot since the absolute value of the slope is issued for the abscissa in the dV/dD plot. FIG. 9 shows the dV/dD plot.

Using the slope of the cumulative pore volume plot as observed in the dV/dD plot to define the cutoff looks more promising than the other options for defining the maximum pore diameter. The dV/dD cutoff of about 0.001 or 0.002 cc/g-Å would give a maximum pore diameter of 55-60 Å, overlapping the range that was initially targeted based on the points at which the adsorption branches of the isotherms meet the desorption branches.

In the case of a dV/dD cutoff for the maximum pore diameter of 0.002 cc/g-Å, the maximum pore diameter of 55 Å occurs at a cumulative pore volume of 0.034 cc/g, or 4.3% of the total mesopore volume. If a lower value is used for the dV/dD cutoff, the volume in pores greater than the cutoff will be smaller but not by a large amount. For instance if 0.001 cc/g-Å is used for the dV/dD cutoff, there is still 3.2% of the porosity in pores greater than the maximum pore diameter of 61 Å. Furthermore, the maximum pore diameters determined using a cutoff of 0.001 cc/g-Å are not as reproducible as the diameters determined using a cutoff of 0.002 cc/g-Å.

Determine Whether Killer Pores are Present Using the Definition of Killer Pores for Low κ Interlevel Dielectrics for a Specific Node For porous low κ films used as interlevel dielectrics in integrated circuit devices "killer pores" result in catastrophic failure resulting from dielectric breakdown or shorting via Cu ion migration. It is desirable to keep the pores dimensions smaller than the lateral dimensions or feature size in the interlayer dielectric film. The absence of "killer pores" will minimize the possibility of catastrophic failure resulting from dielectric breakdown or shorting via Cu ion migration. Some have assumed that the killer pore size is equal to the critical defect size. The critical defect size is generally ½ the line width. Since the pore size depends on the procedure/model used to calculate the pore size distribution and the method chosen for defining the maximum pore diameter, the actual value for killer pore diameter will need to be determined by correlating the ability to survive integration with maximum pore diameter calculated using a given method.

Since the ASAP BJH calculation using the Kelvin model is known to underestimate the pore diameter, perhaps a killer pore diameter calculated by ASAP BJH might be one fifth of the critical defect size, or 10% of the feature size. Thus if these 1.9 κ films were used at the 65 nm technology node, the size for killer pores calculated by ASAP BJH software might be 65 Å. In that case, one could say that the 1.9 κ film prepared using Triton X-114 surfactant as the porogen, which has a maximum pore diameter as calculated using ASAP BJH and using a cutoff of 0.002 cc/g-Å, of 55 Å, does not have any killer pores within the absence detection limit of the method, which in this case corresponds to about 4.3% of the total mesopore volume. Comparing the maximum pore diameter of 67 Å determined for the L-101 film in the same way to the killer pore diameter of 65 Å, one can determine that the L-101 film would have killer pores, or at best be borderline, with a killer pore volume absence detection limit of 5.2% of the total mesopore volume.

Even if a slope of 0.001 cc/g-Å were chosen as the cutoff, the maximum pore diameter of 61 Å calculated using the ASAP BJH software for the film prepared using X-114 would indicate that there are no killer pores; the absence detection limit would be slightly better at 3.2% of the total porosity. The maximum pore diameter of 71 Å determined in the same way for the film prepared using L-101 would indicate that there are killer pores present (with a killer pore volume absence detection limit of 4.5% of the total mesopore volume).

Example 2

Spin-on Low κ Film using Surfactant as Porogen and GAI/DFT as Procedure/model for Capillary Condensation This example shows the unexpected benefit of DFT over BJH in giving a lower killer pore volume absence detection limit. The samples and isotherms were the same as those used in Example 1.

Calculate the Incremental Pore Volume as a Function of Pore Diameter from the Volumetrically Measured Adsorption Isotherm using GAI as the Procedure and Incorporating DFT as the Model that Relates Pressure for Capillary Condensation to Pore Size Micromeritics ASAP DFT Plus® for Windows, Version 3.00 software, commercially available, was used to calculate the pore size distributions using the $N_2$ adsorption branch of the isotherms at 77 K. The options for the calculations include the choice of model (or kernel of isotherms (to be used in the GAI equation) obtained from the DFT calculations), the extent of regularization (or smoothing), and the data points in the isotherm used for the calculation. The kernel was $N_2$ at 77K, Cylindrical Pores in an Oxide Surface from the DFT Plus® Optional Model Kit Version 2.00. The calculations were performed with no regularization (lambda=0). Isotherm data points were used up to a $P/P_0$ of 0.95.

The convention for the DFT software is to sum the incremental pore volume starting with the smallest pore diameters first to give the plot of cumulative pore volume vs. pore diameter, in contrast to the convention for the BJH calculations, which sums the incremental volumes starting with the larges pore diameters first.

Determine a Maximum Pore Diameter from the Incremental Pore Volume as a Function of Pore Diameter Based on slope of 0.002 cc/g-Å, the film based on X-114 has a maximum pore diameter 74.4 Å. Out of a total pore volume of 0.8589 cc/g, 0.8558 cc/g is in pores with diameter less than 74.4 Å. Thus only 0.36% of the pore volume is in pores larger than the maximum pore diameter. The film based on L-101 has a maximum pore diameter of 87.8 Å. Out of a total pore volume of 0.9483 cc/g, 0.9463 cc/g is in pores with a diameter less than 87.8 Å. Thus only 0.21% of the pore volume is in pores larger than the maximum pore diameter.

The cumulative pore volume plot was obtained by matching the experimental isotherm using the GAI equation. The experimental isotherm was interpolated to match the discrete values of $P/P_0$ in the GAI equation. FIG. 10 compares the adsorption branch of the isotherm calculated using DFT to the experimental isotherm for $N_2$ at 77 K on the 1.9 κ film prepared using Triton X-114 surfactant as the porogen. The fit for the $N_2$ isotherm for the 1.9 κ film prepared using Triton X-114 surfactant as the porogen is relatively good at relative pressures of about 0.3 and greater. The fit at $P/P_0$ above 0.7 supports the statements made above that all of the gradual slope in the isotherm can be accounted for by DFT by compression of $N_2$ condensed in the pores. However, the fit for the low pressure region is not quite as good. The most likely reason why the fit is higher than the experimental isotherm in the low pressure region is that the material has a more weakly interacting surface than the hydroxylated silica used to parameterize the DFT kernel. This explanation is consistent with the expected hydrophobic nature of the surface because of the incorporation of methyl groups from methyltriethoxysilane (MTES) used in the formulation. However, it may not affect the fit at high $P/P_0$ and the killer pore volume absence detection limit.

FIG. 11 provides a comparison of the experimental points to the fitted points for the film prepared using Pluronic L-101 surfactant as the porogen results in the same observations and conclusions.

Determine Whether Killer Pores are Present Using the Definition of Killer Pores for Low κ Interlevel Dielectrics for a Specific Node Since the ASAP DFT calculation would be expected to give a better estimate the pore diameter, perhaps a killer pore diameter calculated by ASAP DFT might be 15% of the feature size. Thus if these 1.9 κ films were used at the 65 nm technology node, the size for killer pores calculated by ASAP DFT software might be 98 Å. In that case, one could say that the 1.9 κ film prepared using Triton X-114 surfactant as the porogen, which has a maximum pore diameter as calculated using ASAP DFT and using a cutoff of 0.002 cc/g-Å, does not have any killer pores within the absence detection limit of the method, which in this case corresponds to about 0.36% of the total mesopore volume. Comparing the maximum pore diameter of 88 Å determined for the L-101 film in the same way to the killer pore diameter of 98 Å, one would determine that the L-101 film would not have killer pores, with a killer pore volume absence detection limit of 0.21% of the total mesopore volume. Thus one can say that the film does not have any killer pores within the absence detection limit of the method. In both cases, the killer pore volume absence detection limit determined from a slope of 0.002 cc/g-Å using DFT is an order of magnitude lower than that using BJH.

Use of a model for capillary condensation that accounts for compression of the adsorbate capillary condensed in the pores, such as Density Functional Theory (DFT), allows quantification of the maximum pore diameter without complications from apparent porosity from the gradual slope in the isotherm at high $P/P_0$. Even though it might seem obvious to use DFT to calculate the pore size distribution from the adsorption isotherm of a porous film, it is not obvious that DFT offers a benefit in detecting killer pores by lowering the killer pore volume absence detection limit. Put another way, DFT is known in the art but it is employed in a novel manner in the present invention.

Another method for determining whether killer pores are present might be to use a definition of maximum pore diameter determined from an absolute volume of pores rather than the slope in the dV/dD plot. There is no volume in pores greater than the discrete pore diameters in the DFT calculations of 82.8 Å for the film based on X-114, and 96.4 Å for the film based on L-101. Thus if the same value of killer pores of 98 Å (15% of the line width) would be used for this method, one would determine that the film based on X-114 would have no killer pores, and the film based on L-101 would be borderline.

REFERENCES

1. Kondoh, E.; Baklanov, M. R.; Lin, E.; Gidley, D.; Nakashima, A. "Comparative Study of Pore Size of Low-Dielectric-Constant Porous Spin-on-Glass Films Using Different Methods of Nondestructive Instrumentation"; Jpn. J. Appl. Phys. 2001, 40, L323-L326.
2. Lee, H.-J.; Soles, C. L.; Liu, D.-W.; Bauer, B. J.; Wu, W.-L. "Pore Size Distributions in Low-k Dielectric Thin Films from X-ray Porosimetry"; J. Polymer Sci. B: Polymer Phys. 2002, 40, 2170-2177.
3. Hietala, S. L.; Smith, D. M.; Hietala, V. M.; Frye, G. C.; Martin, S. J. "Pore Structure Characterization of Thin Films Using a Surface Acoustic WaveNolumetric Adsorption Technique"; Langmuir 1993, 9, 249-51.
4. Baklanov, M. R.; Mogilnikov, K. P.; Polovkinkin, V. G.; Dultsev, F. N. J. Vac. Sci. Technol. B 2000, 18, 1385.
5. Kondoh, E.; Baklanov, M. R.; Lin, E.; Gidley, D.; Nakashima, A. "Comparative Study of Pore Size of Low-Dielectric-Constant Porous Spin-on-Glass Films Using Different Methods of Nondestructive Instrumentation"; Jpn. J. Appl. Phys. 2001, 40, L323-L326.
6. Gidley, D. W.; Frieze, W. E.; Dull, T. L.; Sun, J.; Yee, A. F.; Nguyen, C. V.; Yoon, D. Y. "Determination of Pore-Size Distribution in Low-Dielectric Thin Films"; Appl. Phys. Lett. 2000, 76, 1282-1284.
7. Dull, T. L.; Frieze, W. E.; Gidley, D. W.; Sun, J. N.; Yee, A. F. "Determination of Pore Size in Mesoporous Thin Films from the Annihilation Lifetime of Positronium"; J. Phys. Chem. B 2001, 105, 4657-4662.
8. Wu, W.-L.; Wallace, W. E.; Lin, E. K.; Lynn, G. W.; Glinka, C. J.; Ryan, E. T.; Ho, H.-M. M. "Properties of nanoporous silica thin films determined by high-resolution x-ray reflectivity and small-angle neutron scattering"; J. Appl. Phys. 2000, 87, 1193-1200.
9. Wormington, M. "X-ray Reflectivity from Porous Low-κ Dielectric Thin-Films on Si Substrates"; received by J. B. Higgins from Bede Scientific Inc.
10. Frye, G. C.; Ricco, A. J.; Martin, S. J.; Brinker, C. J. "Characterization of the Surface Area and Porosity of Sol-gel Films using SAW Devices"; Mater. Res. Soc. Symp. Proc. 1988, 121, 349.
11. Baklanov, M. R.; Dultsev, F. N.; Mogilnikov, K. P.; Maex, K. "Apparatus and Method for Determining Porosity"; U.S. Pat. No. 6,319,736 B1, 2001.
12. Baklanov, M. R.; Dultsev, F. N.; Mogilnikov, K. P.; Maex, K. "Apparatus and Method for Determining Porosity"; U.S. Pat. No. 6,435,008 B2, 2002.
13. Baklanov, M. R.; Mogilnikov, K. P.; Maex, K.; Shamiryan, D.; Dultsev, F. N. "Method and Apparatus for Characterization of Porous Films"; U.S. patent application 2003/0094032 A1, 2003.
14. Thommes, M. "Pore Size Analysis by Gas Adsorption. Part I: Aspects of the Application of Density Functional Theory (DFT) and Monte Carlo Simulation (MC) for Micro/Mesopore Size Analysis"; Quantachrome Powder Tech Note 31.
15. Terada, S.; Masaki, M. "X-ray Analyzing Apparatus and X-ray Irradiation Angle Setting Method"; U.S. Pat. No. 5,949,847, 1999.
16. Wormington, M.; Panaccione, C.; Matney, K. M.; Bowen, D. K. "Fitting of X-ray Scattering Data using Evolutionary Algorithms"; U.S. Pat. No. 6,192,103 B1, 2001.
17. Killip, G. R.; Camp, R. W.; Orr, Jr., C. "Temperature Controlling Apparatus for Use with Pore Volume and Surface Area analyzers"; U.S. Pat. Re. 33,567, 1991, reissue of U.S. Pat. No. 4,693,124, 1987.
18. Thomas, M. A.; Novella, N. N.; Lowell, S. "Method for Compensating for the Time-Dependent Change in Coolant Level During Gas Sorption Analysis"; U.S. Pat. No. 6,387,704 B1, 2002.

19. Wenman, R. A.; Fong, J. "Wickless Temperature Controlling Apparatus and Method for Use with Pore Volume and Surface Area Analyzers"; U.S. Pat. No. 5,646,335, 1997.
20. IUPAC Manual of Symbols and Terminology, Appendix 2, Pt. 1, colloid and Surface Chemistry; *Pure Appl. Chem.* 1972, 31, 578.
21. Rouquerol, F.; Rouquerol, J.; Sing, K. *Adsorption by Powders and Porous Solids;* Academic Press: London, 1999, pp.199, 219.
22. Cohan, L. H. "Sorption Hysteresis and the Vapor Pressure of Concave Surfaces"; *J. Am. Chem. Soc.* 1938, 60, 433-435.
23. FIG. 3.4 from Webb, P. A.; Orr, C. *Analytical Methods in Fine Particle Technology;* Micromeritics Instrument Corporation: Norcross, Ga., 1997.
24. Halsey, G. "Physical Adsorption on Non-Uniform Surface"; *J. Chem. Phys.* 1948, 16, 931-937.
25. Harkins, W. D.; Jura, G. *J. Chem. Phys.* 1943, 11, 431.
26. Kruk, M.; Jaroniec, M.; Sayari, A. "Application of Large Pore MCM-41 Molecular Sieves To Improve Pore size Analysis Using Nitrogen Adsorption Measurements"; *Langmuir* 1997, 13, 6267-6273.
27. "Standard Practice for Calculation of Pore Size Distributions of Catalysts from Nitrogen Desorption Isotherms"; ASTM Designation D4641-94(Reapproved 1999), *Annual Book of ASTM Standards,* Vol. 05.03.
28. Table 10.2 in Rouquerol, F.; Rouquerol, J.; Sing, K. *Adsorption by Powders and Porous Solids;* Academic Press: London, 1999.
29. Jaroniec, M.; Kruk, M.; Olivier, J. P. "Standard Nitrogen Adsorption Data for Characterization of Nanoporous Silicas"; Langmuir 1999, 15, 5410-5413.
30. Kruk, M.; Antochshuk, V.; Jaroniec, M.; Sayari, A. "New Approach to Evaluate Pore Size Distributions and Surface Areas for Hydrophobic Mesoporous Solids"; *J. Phys. Chem. B* 1999, 103, 10670-10678.
31. Barrett, E. P.; Joyner, L. G.; Halenda, P. P. "The Determination of Pore Volume and Area Distributions in Porous Substances. I. Computations from Nitrogen Isotherms"; *J. Am. Chem. Soc.* 1951, 73, 373-380.
32. Brunauer, S.; Mikhail, R. Sh.; Bodor, E. E. "Pore Structure Analysis without a Pore Shape Model"; *J. Colloid Interface Sci.* 1967, 24, 451-463.
33. Dubinin, M. M.; Radushkevich, L. V. *Proc. Acad. Sci. USSR* 1947, 55, 331.
34. Cranston, R. W.; Inkley, F. A. "The Determination of Pore Structures from Nitrogen Adsorption Isotherms"; *Advances in Catalysis;* Academic Press: New York, 1957; Vol. 9, pp 143-154.
35. Neimark, A. V.; Ravikovitch, P. I. "Capillary condensation in MMS and pore structure characterization"; *Microporous Mesoporous Mater.* 2001, 44-45, 697-707.
36. FIG. 1 from Neimark, A. V.; Ravikovitch, P. I. "Capillary condensation in MMS and pore structure characterization"; *Microporous Mesoporous Mater.* 2001, 44-45, 697-707.
37. Ohkubo, T.; Miyawaki, J.; Kaneko, K.; Ryoo, R.; Seaton, N. A. "Adsorption Properties of Templated Mesoporous Carbon (CMK-1) for Nitrogen and Supercritical Methane—Experimental and GCMC Simulation"; *J. Phys. Chem. B* 2002, 106, 6523-6528.
38. Wormington, M. "X-ray Reflectivity from Porous Low-κ Dielectric Thin-Films on Si Substrates"; Bede Scientific Inc.
39. Iacoponi, J. "Status and Future Prospects for Low κ Interconnect Metrology"; presentation at International SEMATECH, Mar. 25, 2003. URL: http://www.eeel.nist.gov/812/conference/Presentations/Iacoponi.pdf.
40. Groen, J. C.; Peffer, L. A. A.; Perez-Ramirez, J. "Pore size determination in modified micro-and mesoporous materials. Pitfalls and limitations in gas adsorption data analysis"; *Microporous Mesoporous Mater.* 2003, 60, 1-17.

We claim:

1. A method for determining a presence of at least one killer pore contained within a porous film deposited upon a substrate wherein a pore size of the at least one killer pore is equal to or greater than a reference pore size, the method comprising:
    a. providing the substrate having the film deposited thereupon wherein the film comprises pores and wherein the pores have a first volume;
    b. exposing the film to an adsorbate at a temperature and a pressure sufficient to provide condensation of the adsorbate in pores and wherein the pores after the exposing step have a second volume;
    c. measuring the difference between the first and the second volume;
    d. repeating steps b and c wherein the condensed adsorbate has a different density than the previous exposure;
    e. calculating the pore size and volume for each exposure using the difference in the first and the second volume, the pressure, and a model that relates pressure to pore diameter and accounts for the change in density of the condensed adsorbate;
    f. obtaining a maximum pore size from the distribution; and
    g. determining the presence of at least one killer pore by comparing the maximum pore size to a reference pore size.

2. The method of claim 1 wherein the model in the calculating step comprises density function theory.

3. The method of claim 1 wherein the obtaining step comprises using one selected from an absolute pore volume cutoff, a percent pore volume cutoff, and a cutoff pore distribution slope.

4. The method of claim 3 wherein the obtaining step comprises the absolute pore volume cutoff.

5. The method of claim 3 wherein the obtaining step comprises the percent pore volume cutoff.

6. The method of claim 3 wherein the obtaining step comprises a cutoff pore distribution slope.

* * * * *